United States Patent [19]

Matsuo, deceased et al.

[11] Patent Number: 4,560,508

[45] Date of Patent: Dec. 24, 1985

[54] 4-CYANO-2-AZETIDINONES AND PRODUCTION THEREOF

[75] Inventors: Taisuke Matsuo, deceased, late of Osaka, by Michiko Matsuo, Takeshi Matsuo, Tazuko Matsuo, heirs; Michihiko Ochiai, Osaka; Shoji Kishimoto, Hyogo, all of Japan

[73] Assignee: Takeda Chemical Industries, Ltd., Osaka, Japan

[21] Appl. No.: 451,323

[22] Filed: Dec. 20, 1982

[30] Foreign Application Priority Data

Dec. 25, 1981 [JP] Japan ................. 56-212718
Apr. 27, 1982 [WO] PCT Int'l Appl. ..... PCT/JP8200141

[51] Int. Cl.$^4$ ................. C07D 205/08; C07D 403/12; C07D 401/12; A61K 31/395

[52] U.S. Cl. ........................... 260/239 A; 260/245.4; 260/330.3; 260/330.9; 544/90; 544/238; 544/229; 544/279; 544/295; 544/296; 544/298; 544/300; 544/301; 544/310; 544/311; 544/316; 544/317; 544/319; 544/320; 544/321; 544/322; 544/323; 544/324; 544/325; 544/327; 544/331; 544/332; 544/333; 544/334; 544/335; 544/336; 544/337; 544/359; 544/360; 544/362; 544/363; 544/364; 544/365; 544/366; 544/367; 544/369; 544/370; 544/371; 544/372; 544/374; 544/377; 544/379; 544/405; 544/406; 544/407; 544/408; 544/409; 546/14; 546/114; 546/122; 546/123; 546/153; 546/155; 546/156; 546/157; 546/159; 546/162; 546/187; 546/193; 546/194; 546/197; 546/208; 546/209; 546/210; 546/211; 546/256; 546/261; 546/263; 546/264; 546/270; 546/275; 546/276; 546/277; 546/278; 546/279; 546/280; 546/281

[58] Field of Search ............. 260/239 A, 245.4, 330.3, 260/330.9; 544/90, 238, 229, 279, 295, 296, 298, 300, 301, 310, 311, 316, 317, 319, 320, 321, 322, 323, 324, 325, 327, 331, 332, 333, 334, 335, 336, 337, 359, 360, 362, 363, 364, 365, 366, 367, 369, 370, 371, 372, 374, 377, 379, 405, 406, 407, 408, 409; 546/14, 114, 122, 123, 153, 155, 156, 157, 159, 162, 187, 193, 194, 197, 208, 209, 210, 211, 256, 261, 263, 264, 270, 275, 276, 277, 278, 279, 280, 281

[56] References Cited

U.S. PATENT DOCUMENTS 4,166,816  9/1979  Gleason et al. ................. 260/239 A
4,200,572  4/1980  Gleason et al. ................. 260/239 A
4,416,817 11/1983  Matsuo et al. ................. 260/239 A

FOREIGN PATENT DOCUMENTS 3148021 10/1982  Fed. Rep. of Germany .
2017650  9/1981  United Kingdom .
2087394  5/1982  United Kingdom .

OTHER PUBLICATIONS

Hubschnerlen, Chem. Abs., 99, 38291c (1983).

Primary Examiner—Mark L. Berch
Attorney, Agent, or Firm—Wenderoth, Lind & Ponack

[57] ABSTRACT

4-Cyano-2-azetidinone derivatives represented by the formula

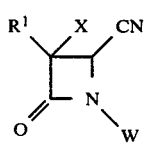

wherein $R^1$ is an amino group which may be acylated or protected, X is a hydrogen atom or a methoxy group and W is a hydrogen atom or a sulfo group, and methods of producing the same, for example, as represented by

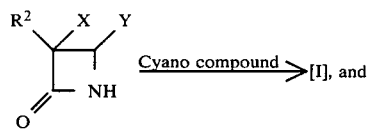

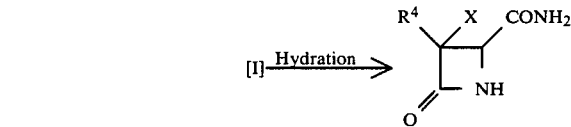

wherein $R^2$ is an acylated or protected amino group, Y is a halogen atom or a group having the formula —OCOR$^3$, —SCOR$^3$ or —S(O)$_n$—R$^3$ (R$^3$ being a hydrocarbyl group and n an integer 1 or 2), R$^4$ is an amino group which may be acylated or protected and X is as defined above. Compounds [I] are useful as advantageous intermediates for the synthesis of optically active 4-substituted-2-azetidinone derivatives, and, when W=SO$_3$H, [I] are also useful as antimicrobial agents and as beta-lactamase inhibitors.

9 Claims, No Drawings

4-CYANO-2-AZETIDINONES AND PRODUCTION THEREOF

TECHNICAL FIELD

This invention relates to a new class of 4-cyano-2-azetidinone derivatives which are useful for the synthesis of optically active forms of 4-substituted-2-azetidinone derivatives and some of which have antimicrobial and β-lactamase-inhibitory activity, a method of producing said class of derivatives, and a method of using them as synthetic intermediates.

BACKGROUND TECHNOLOGY

Recently, a new class of β-lactam antibiotic compounds having a sulfo group in 1-position have been found to be recoverable from nature sources and reported [Nature 289, 590 (1981), 291, 489 (1981)]. Synthesis of compounds related thereto has also been reported (e.g. EP-A1-0021678 and EP-A1-0048953). The latter literature teaches a method of synthesizing 2-azetidinone-1-sulfonic acid compounds having a substituent in 4-position but the method involves a long series of reaction steps and no expedient process for the purpose has been reported.

DISCLOSURE OF THE INVENTION

This invention relates to a novel class of 4-cyano-2-azetidinone derivatives having the formula:

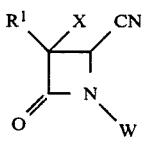

[R$^1$ is an amino group which may optionally be acylated or protected; X is H or methoxy; W is H or sulfo], a method for producing said derivatives [I] and a method of using them [I] as synthetic intermediates.

The research undertaken by the present inventors led to the finding that if a compound of the formula:

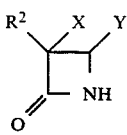

[R$^2$ is an acylated or protected amino group; Y is halogen or a group of the formula —OCOR$^3$, —SCOR$^3$ or

(R$^3$ is hydrocarbyl; n is an integer of 1 or 2); X has the meanings defined above] is reacted with a cyano compound and thus obtained compound [I] wherein W is H may optionally be further sulfonated to obtain compound [I] wherein W is sulfo, and, if necessary, the amino-protecting group is eliminated, there is obtained a 4-cyano-2-azetidinone derivative [I] and that this derivative [I] is useful as an intermediate for the synthesis of 4-substituted-2-azetidinone derivatives and particularly of optionally active forms thereof. To elaborate on the latter finding, it was found that if the compound [I] is hydrated and, if necessary, the amino-protecting group is eliminated, there is obtained a 4-carbamoyl-2-azetidinone derivative of the formula:

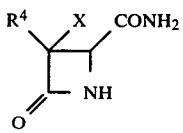

[R$^4$ is an acylated or protected amino group; X has the meanings defined above]. This invention has been conceived and developed on the basis of the above findings.

Referring to the above formulas, the acyl moiety of the acylated amino group R$^1$, R$^2$, R$^4$ may for example be one of those acyl groups substituting the 6-amino groups of the known penicillin derivatives or the 7-amino groups of the known cephalosporin derivatives. Specific examples of such acyl groups include, among others, (1) groups of the formula:

$$R^5\text{—CO—} \quad [A]$$

[R$^5$ is lower alkyl, optionally substituted phenyl or optionally substituted heterocyclic group], (2) groups of the formula:

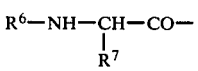

[R$^6$ is H, optionally substituted amino acid residue, amino-protecting group or a group of the formula R$^8$13 (CH$_2$)$_m$—CO— (R$^8$ is amino, optionally substituted heterocyclic group, optionally substituted phenyl or optionally substituted lower alkyl; m is an integer of 0 to 3); R$^7$ is H, optionally substituted lower alkyl, optionally substituted phenyl, optionally substituted heterocyclic group or optionally substituted cycloalkenyl]; (3) groups of the formula

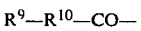

$$R^9\text{—}R^{10}\text{—CO—} \quad [C]$$

[R$^9$ is a group of the formula

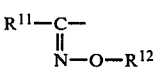

(R$^{11}$ is optionally substituted heterocyclic group or optionally substituted phenyl; R$^{12}$ is H, optionally substituted phenyl, lower acyl, lower alkyl or a group of the formula —R$^{13}$—R$^{14}$ (R$^{13}$ is lower alkylene or lower alkenylene; R$^{14}$ is carboxy or esterified carboxy); R$^{10}$ is a bond or a group of the formula

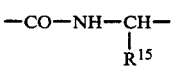

(R$^{15}$ is lower alkyl or optionally substituted heterocyclic group)]; (4) groups of the formula:

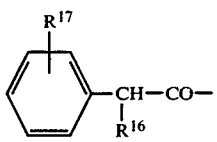
[D]

[$R^{16}$ is hydroxy, carboxy, sulfo, formyloxy, halo or azido; $R^{17}$ is H, lower alkyl, lower alkoxy, halo or hydroxy]; and (5) groups of the formula:

[E]

[$R^{18}$ is cyano, optionally substituted phenyl, optionally substituted phenoxy, optionally substituted lower alkyl, optionally substituted alkenyl or optionally substituted heterocyclic group; $R^{19}$ is a bond or —S—].

Referring to $R^5$ through $R^{19}$ in the above formulas [A] through [E], the lower alkyl group is a group of 1 to 6 carbon atoms, such as methyl, ethyl, n-propyl, isopropyl, n-butyl, isobutyl, sec-butyl, tert-butyl, pentyl, isopentyl, hexyl, isohexyl, etc.

The lower alkoxy includes $C_{1-6}$ alkoxy groups such as methoxy, ethoxy, n-propoxy, isopropoxy, n-butoxy, isobutoxy, sec-butoxy, tert-butoxy, pentoxy, isopentoxy, hexyloxy, and isohexyloxy. The alkenyl includes vinyl, allyl, isopropenyl, 2-methallyl, 2-butenyl and 3-butenyl. The cycloalkenyl is preferably of the 5- or 6-membered ring, for example, cyclohexenyl and cyclohexadienyl. The lower alkylene preferably contains 1–3 carbon atoms and is, for example, methylene, dimethylene, ethylene, methylethylene or trimethylene. The lower alkylene preferably contains 1–3 carbon atoms and is, for example, vinylene or propenylene. Examples of the halogen are chlorine, bromine, iodine, and fluorine.

The heterocyclic group includes, among others, 5- to 8-membered rings containing 1 to a few hetero atoms such as N (which may form an oxide), O and S, as well as fused ring structures involving such rings, which are bonded through a carbon atom thereof. Thus, for example, frequently used are such heterocyclic groups as 2- or 3-pyrrolyl, 2- or 3-furyl, 2- or 3-thienyl, 2- or 3-pyrrolidinyl, 2-, 3- or 4-pyridyl, N-oxido-2-, 3- or 4-pyridyl, 2-, 3- or 4-piperidinyl, 2-, 3- or 4-pyranyl, 2-, 3- or 4-thiopyranyl, pyrazinyl, 2-, 4- or 5-thiazolyl, 2-, 4- or 5-oxoazolyl, 3-, 4- or 5-isothiazolyl, 3-, 4- or 5-isoxazolyl, 2-, 4- or 5-imidazolyl, imidazolidinyl, 3-, 4- or 5-pyrazolyl, pyrazolidinyl, 3- or 4-pyridazinyl, N-oxido-3- or 4-pyridazinyl, 2-, 4- or 5-pyrimidinyl, N-oxido-2-, 4- or 5-pyrimidinyl, piperazinyl, 4- or 5-(1,2,3-thiadiazolyl), 3- or 5-(1,2,4-thiadiazolyl), 1,3,4-thiadiazolyl, 1,2,5-thiadiazolyl, 4- or 5-(1,2,3-oxoadiazolyl), 3- or 5-(1,2,4-oxadiazolyl), 1,3,4-oxadiazolyl, 1,2,5-oxadiazolyl, 1,2,3- or 1,2,4-triazolyl, 1H- or 2H-tetrazolyl, pyrido(2,3-d)-pyrimidyl, benzopyranyl, 1,8-, 1,5-, 1,6-, 1,7-, 2,7- or 2,6-naphthyridyl, quinolyl, thieno(2,3-b)pyridyl, etc. The amino acid residue includes glycyl, alanyl, valyl, leucyl, isoleucyl, seryl, threonyl, cysteinyl, cystyl, methionyl, α- or β-aspartyl, α- or β-glutamyl, lysyl, arginyl, phenylalanyl, phenylglycyl, tyrosyl, histidyl, tryptophyl, and prolyl. The amino-protecting group includes those to be mentioned hereinbelow. The lower acyl preferably contains 2–4 carbon atoms and is, for example, acetyl, propionyl, butyryl, or isobutyryl. The substituent for the optionally substituted lower alkyl and for the optionally substituted alkenyl includes phenyl, carbamoyl, methylcarbamoyl, carboxy, cyano, halogen, hydroxy, etc. The substituents for the optionally substituted phenyl, phenoxy and cycloalkenyl include $C_{1-3}$ lower alkyl, $C_{1-3}$ lower alkoxy, halogen, amino, benzyloxy, hydroxy, $C_{2-10}$ acyloxy, aminomethyl, carbamoylaminomethyl, 3-amino-3-carboxypropoxy, etc. The substituent for the optionally substituted heterocyclic group includes optionally substituted $C_{1-8}$ alkyl, $C_{1-3}$ lower alkoxy, hydroxy, carboxy, oxo, monochloroacetamido, aldehyde, trifluoromethyl, amino, halogen, optionally substituted phenyl such as mentioned above (e.g. 2,6-dichlorophenyl), coumarin-3-carbonyl, 4-formyl-1-piperazinyl, pyrrolealdimino, furanaldimino, thiophenealdimino, mesyl, mesylamino, amino-protecting groups, optionally halo-substituted $C_{2-4}$ acylamino, etc. The amino-protecting groups include those to be mentioned hereinbelow. The optionally substituted amino acid residue includes amino, amino-protecting groups, carbamoyl, methylcarbamoyl, and benzyl. The amino-protecting groups include those to be mentioned hereinbelow. The esterified carboxy group $R^{14}$ includes methyl ester, ethyl ester, propyl ester, t-butyl ester, p-nitrobenzyl ester and 2-trimethylsilylethyl ester.

Amino, carboxy or/and hydroxy groups, if any, in the above-mentioned substituents $R^5$ through $R^{19}$ may be protected. The amino-protecting groups in such cases may for example be "the amino-protecting groups" mentioned hereinafter for $R^1$. The carboxy-protecting groups may be any and all groups which are commonly used for the protection of carboxy functions in β-lactam or organic chemistry. Thus, for example, methyl, ethyl, n-propyl, isopropyl, tert-butyl, tert-amyl, benzyl, p-nitrobenzyl, p-methoxybenzyl, benzhydryl, phenacyl, phenyl, p-nitrophenyl, methoxymethyl, ethoxymethyl, benzyloxymethyl, acetoxymethyl, pivaloyloxymethyl, β-methylsulfonylethyl, methylthiomethyl, trityl, β,β,β-trichloroethyl, β-iodoethyl, 2-trimethylsilylethyl, trimethylsilyl, dimethylsilyl, acetylmethyl, p-nitrobenzoylmethyl, p-mesylbenzoylmethyl, phthalimidomethyl, propionyloxymethyl, mesylmethyl, benzenesulfonyl- methyl, phenylthiomethyl, ester residues (e.g. dimethylaminoethyl) and silyl are used. Especially preferred are β,β,β-trichloroethyl, p-nitrobenzyl, tert-butyl, 2-trimethylsilylethyl and p-methyoxybenzyl. The hydroxy-protecting group may be any and all groups which are commonly employed for the protection of hydroxy functions in β-lactam or organic chemistry. Thus, for example, there may be mentioned ester residues such as acetyl, chloroacetyl, etc., esterified carboxy groups such as β,β,β-trichloroethoxycarbonyl, 2-trimethylsilylethoxycarbonyl, etc., ether residues such as tert-butyl, benzyl, p-nitrobenzyl, trityl, methylthiomethyl, β-methoxyethoxymethyl, etc., silyl ether residues such as trimethylsilyl, tert-butyldimethylsilyl, etc., acetal residues such as 2-tetrahydropyranyl, 4-methoxy-4-tetrahydropyranyl, etc. These protective groups may be selected more or less liberally as it is true with amino- and carboxy-protecting groups.

Referring to the acyl groups mentioned earlier, the acyl group $R^5$—CO—[A] may for example be 3-(2,6-dichlorophenyl)-5-methylisooxazol-4-yl-carbonyl.

Among specific examples of the acyl group

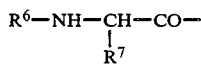
[B]

are D-alanyl, D-phenylalanyl, α-benzyl-N-carbobenzoxy-γ-D-glutamyl-D-alanyl, D-phenylglycyl-D-alanyl, N-carbobenzoxy-D-phenylglycyl, D-alanyl-D-phenylglycyl, γ-D-glutamyl-D-alanyl, N-carbobenzoxy-D-alanyl-D-phenylglycyl, D-carbamoyltryptophyl-D-phenylglycyl, N-[2-amino-3-(N-methylcarbamoyl)-propionyl]-D-phenylglycyl, N-carbobenzoxy-D-phenylglycyl-D-phenylglycyl, D-alanyl-D-alanyl, 2-[2-amino-3-(N-methylcarbamoyl)propionamido]acetyl, D-2-(4-ethyl-2,3-dioxo-1-piperazinecarboxamido)-2-(4-methoxyphenyl)acetyl, D-2-[2-(4-ethyl-2,3-dioxo-1-piperazinecarboxamido)acetamido]-2-phenylacetyl, 2-(2-aminothiazol-4-yl)-2-(4-ethyl-2,3-dioxo-1-piperazinecarboxamindo)acetyl, D-2-(4-ethyl-2,3-dioxo-1-piperazinecarboxamido)-2-thienylacetyl, D-2-(4-n-dodecyl-2,3-dioxo-1-piperazinecarboxamido)-2-phenylacetyl, D-2-(4,6-diethyl-2,3-dioxo-1-piperazinecarboxamido)-2-phenylacetyl, D-2-(4-cyclohexyl-2,3-dioxo-1-piperazinecarboxamido)-2-thienylacetyl, D-2-(4-n-amyl-6(S)-methyl-2, D-3-dioxo-1-piperazinecarboxamido)-2-thienylacetyl, D-2-(4-ethyl-5-methyl-2,3-dioxo-1-piperazinecarboxamido)-2-thienylacetyl, D-2-(8-hydroxy-1,5-naphthyridine-7-carboxamido)-2-phenylacetyl, D-2-(4-n-octyl-2,3-dioxo-1-piperazinecarboxamido)-2-phenylacetyl, 2-(4-ethyl-2,3-dioxo-1-piperazinecarboxamido)-2-(4-chlorophenyl)acetyl, α-N-(4-ethyl-2,3-dioxo-1-piperazinecarbonyl)-glutaminyl, D-N-(4-ethyl-2,3-dioxo-1-piperazinecarbonyl)phenylalanyl, D-2-(4-ethyl-2,3-dioxo-1-piperazinecarboxamido)-2-(4-hydroxyphenyl)acetyl, 2-(4-ethyl-2,3-dioxo-1-piperazinecarboxamido)-2-(1-cylohexen-1-yl)acetyl, D-2-(4-n-octyl-2,3-dioxo-1-piperazinecarboxamido)-2-thienylacetyl, 2-(4-ethyl-2,3-dioxo-1-piperazinecarboxamido)-2-(2-methylthiazol-4-yl)acetyl, 2-(4-n-octyl-2,3-dioxo-1-piperazinecarboxamido)-2-(2-aminothiazol-4-yl)acetyl, 2-(4-ethyl-2,3-dioxo-1-piperazinecarboxamido)-2-furylacetyl, D-2-(4-ethyl-2,3-dioxo-1-piperazinecarboxamido)-2-(2-pyrrolyl)acetyl, D-2-(4-ethyl-2,3-dioxo-1-piperazinecarboxamido)-3-chloropropionyl, D-2-[4-(2-hydroxyethyl)-2,3-dioxo-1-piperazinecarboxamido]-2-phenylacetyl, D-2-[4-(2-chloroethyl)-2,3-dioxo-1-piperazinecarboxamido]-2-phenylacetyl, D-2-[(3-furfurylideneamino-2-oxoimidazolidin-1-yl)carboxamido]-2-phenylacetyl, D-2-[(3-furfurylideneamino-2-oxoimidazolidin-1-yl)carboxamido]-2-(4-hydroxyphenyl)-acetyl, D-2-[[2-oxo-3(thiophene-2-aldimino)imidazolidin-1-yl]carboxamido]-2-phenylacetyl, D-2-[(3-furfurylideneamino-2-oxoimidazolidin-1-yl)carboxamido]-2-thienylacetyl, D-2-[(3-methylsulfonyl-2-oxoimidazolidin-1-yl)carboxamido]-2-phenylacetyl, 2-[(3-furfurylideneamino-2-oxoimidazolidin-1-yl)carboxamido]-2-(2-aminothiazol-4-yl)acetyl, D-2-[[2-oxo-3-(thiophene-2-aldimino)imidazolidin-1-yl]carboxamido-2-thienylacetyl, D-2-(4-hydroxy-6-methylnicotinamido)-2-(4-hydroxyphenyl)acetyl, D-2-[5,8-dihydro-2-(4-formyl-1-piperazinyl)-5-oxopyrido[2,3-d]pyrimidine-6-carboxamido]-2-phenylacetyl, D-2-(3,5-dioxo-1,2,4-triazine-6-carboxamido)-2-(4-hydroxyphenyl)acetyl, D-2-(coumarin-3-carboxamido)-2-phenylacetyl, 2-(4-ethyl-2,3-dioxo-1-piperazinecarboxamido)-2-(2-chloro-1-cyclohexen-1-yl)acetyl, 2-(4-hydroxy-7-trifluoromethylquinoline-3-carboxamido)-2-phenylacetyl, N-[2-(2-aminothiazol-4-yl)acetyl]-D-phenylglycyl, D-2-[[3-(2,6-dichlorophenyl)-5-methylisoxazol-4-yl]carboxamido]-2-thienylacetyl, D-2-(carbamoyl)amino-2-thienylacetyl and N-carbamoyl-D-phenylglycyl. Among specific examples of the acyl group R$^9$-R$^{10}$—CO— [C] are N-[2-(2-aminothiazol-4-yl)-2-methoxyiminoacetyl]-D-alanyl, 2-(2-chloroacetamidothiazol-4-yl)-2-methoxyiminoacetyl, 2-(2-aminothiazol-4-yl)-2-isopropoxyiminoacetyl, 2-(2-aminothiazol-4-yl)-2-methoxyiminoacetyl, 2-(2-aminothiazol-4-yl)-2-oxyiminoacetyl, 2-thienyl-2-methoxyiminoacetyl, 2-furyl-2-methoxyiminoacetyl, 2-(4-hydroxyphenyl)-2-methoxyiminoacetyl, 2-phenyl-2-methoxyiminoacetyl, 2-thienyl-2-oxyiminoacetyl, 2-thienyl-2-dichloroacetyloxyiminoacetyl, 2-[4-(3-amino-3-carboxypropoxy)phenyl]-2-oxyiminoacetyl, 2-(5-chloro-2-aminothiazol-4-yl)-2-methoxyiminoacetyl, 2-(2-aminothiazol-4-yl)-2-(1-carboxymethoxyimino)acetyl, 2-(2-aminothiazol-4-yl)-2-(1-carboxyethoxyimino)acetyl, 2-(2-aminothiazol-4-yl)-2-(1-carboxy-1-methylethoxyimino)acetyl, 2-(2-aminothiazol-4-yl)-2-(1-methoxycarbonyl-1-methylethoxyimino)-acetyl, 2-(2-aminothiazol-4-yl)-2-(1-carboxy-1-cyclopropylmethoxyimino)acetyl, 2-(2-aminothiazol-4-yl)-2-(1-carboxy-1-cyclobutylmethoxyimino)acetyl and 2-(2-aminothiazol-4-yl)-2-(1-carbamoyl-1-methylethoxyimino)acetyl. Among specific examples of the acyl group of the formula

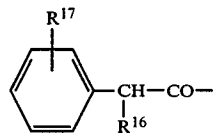

[D]

are α-sulfophenylacetyl, α-hydroxyphenylacetyl, α-formyloxyphenylacetyl, α-carboxyphenylacetyl, 2-bromo-2-phenylacetyl and 2-azido-2-phenylacetyl. Specific examples of the acyl group of the formula R$^{18}$—R$^{19}$—CH$_2$—CO— [E] are cyanoacetyl, phenylacetyl, phenoxyacetyl, trifluoromethylthioacetyl, cyanomethylthioacetyl, 1H-tetrazolyl-1-acetyl, 2-thienylacetyl, 2-(2-aminothiazol-4-yl)acetyl, 2-(2-chloroacetamidothiazol-4-yl)acetyl, 4-pyridylthioacetyl, 3,5-dichloro-1,4-dihydro-4-oxopyridine-1-acetyl, β-carboxyvinylthioacetyl, 2-(2-N-carbobenzoxyaminomethylphenyl)acetyl and 2-(2-ureidomethylphenyl)acetyl.

As the protective groups in the protected amino groups R$^1$, R$^2$ and R$^4$, there may conveniently be used any of those commonly used for the same purpose in the field of beta-lactam chemistry and peptide synthesis. Thus, for example, aromatic acyl groups such as phthaloyl, p-nitrobenzoyl, p-tert-butylbenzoyl, p-tert-butylbenzenesulfonyl, benzenesulfonyl and toluenesulfonyl, aliphatic acyl groups such as formyl, acetyl, propionyl, monochloroacetyl, dichloroacetyl, trichloroacetyl, methanesulfonyl, ethanesulfonyl, trifluoroacetyl, phenylacetyl and succinyl, esterified carboxyl groups as benzyloxycarbonyl, p-nitrobenzyloxycarbonyl, p-methoxybenzyloxycarbonyl, p-nitrobenzyloxycarbonyl, 2-trimethylsilylethoxycarbonyl and methoxycarbonyl, and other amino-protecting groups than acyl groups, such as trityl, 2-nitrophenylthio, benzylidene, 4-nitrobenzylidene, di- or trialkylsilyl, tert-butyldimethylsilyl, tert-butyldiphenylsilyl, benzyl and p-nitrobenzyl may be employed. While these protective groups may be selected liberally as it is true with carboxy-protecting groups, there may be mentioned monochloroacetyl, trityl, benzyloxycarbonyl, p-methoxybenzyloxycarbonyl, 2-trimethylsilylethoxycarbonyl and p-nitrobenzyloxycarbonyl as preferred species.

Y represents a halogen atom or a group of the formula —OCOR$^3$, —SCOR$^3$ or —S(O)$_n$—R$^3$ (R$^3$ is hydrocarbyl which may be substituted; n is equal to 1 or 2). The halogen mentioned above is chlorine, fluorine, iodine or bromine. The hydrocarbyl group includes, among others, such optionally substituted lower alkyl, alkenyl and cycloalkenyl groups as mentioned for $R^5$ through $R^{19}$, cycloalkyl groups containing 3 to 10 carbon atoms such as cyclopropyl, cyclobutyl, cyclopentyl, cyclohexyl, cycloheptyl, adamantyl, etc., aryl groups such as phenyl, tolyl, xylyl, biphenylyl, naphthyl, anthryl, phenanthryl, etc., and aralkyl groups such as benzyl, phenethyl, phenylpropyl, naphthylmethyl, etc. These cycloalkyl, aryl and aralkyl groups may be substituted, in which cases the substituents may be similar to those phenyl- or phenoxy-substituting groups mentioned for $R^5$ through $R^{19}$. Particularly satisfactory results are obtained when Y is for example a lower acyloxy (e.g. acetoxy, propionyloxy) or lower alkylsulfonyl (e.g. methylsulfonyl, ethylsulfonyl) group. X is H or methoxy, and W is H or sulfo.

In accordance with this invention, a compound [II] is reacted with a cyano compound and, if necessary, the protective group is eliminated to give a compound [I].

The compound [II] can be employed in an optional form, whether as the free compound, as salts with various acids or bases, as esters or as silyl derivatives, for instance. For the compound [II] which has substituents at the 3- and 4-positions, there exist the cis- and trans-isomers. Furthermore, the carbon atoms at the 3- and 4-positions are asymmetric carbon atoms. Therefore, there exist theoretically at least 4 steroisomers in total. These stereoisomers may be used either alone or in the form of a mixture. The same applies to the case where the group $R^2$ contains an asymmetric carbon atom. The resulting stereoisomers may be used either alone or in the form of a mixture.

As the salts of compound [II], there may be used, where the compound [II] has a carboxyl group in $R^2$, salts with nontoxic cations such as sodium and potassium, with basic amino acids such as arginine, ornithine, lysine and histidine, and with N-methylglutamine, diethanolamine, triethanolamine, poly(hydroxyalkyl)amines (e.g. tris(hydroxymethyl)aminomethane) and so on. When $R^2$ contains a basic group, there may be used salts with organic acids such as acetic acid, tartaric acid and methanesulfonic acid, salts with inorganic acids such as hydrochloric acid, hydrobromic acid, sulfuric acid and phosphoric acid, salts with acidic amino acids such as arginine, aspartic acid and glutamine, and so forth. When $R^2$ contains a carboxyl group, the compound [II] may also be used after conversion to an ester derivative. The ester group in that case includes, among others, α-alkoxy-α-substituted or unsubstituted-methyl groups such as alkoxymethyl and αalkoxyethyl (e.g. methoxymethyl, methoxyethyl, isopropoxymethyl, α-methoxyethyl, α-ethoxyethyl), alkylthiomethyl groups such as methylthiomethyl, ethylthiomethyl and isopropylthiomethyl, acyloxymethyl and α-acyloxy-α-substituted-methyl groups such as pivaloyloxymethyl and α-acetoxybutyl, and α-alkoxycarbonato-α-substituted-methyl groups such as ethoxycarbonyloxymethyl and α-ethoxycarbonyloxyethyl. The compound [II] may also be used as the starting material in the silylated form produced with the use of a silylating agent. The silylating agent is, for example, a compound of the formula

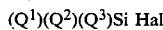 Si Hal wherein $Q^1$, $Q^2$ and $Q^3$ each is a hydrocarbon group such as a lower alkyl containing 1-4 carbon alkyl (e.g. methyl ethyl, n-propyl, i-propyl, n-butyl) or an aryl (e.g. phenyl, tolyl) and Hal is a halogen atom, preferably a chlorine or bromine atom, and wherein one or two of $Q^1$, $Q^2$ and $Q^3$ each may preferably be a chlorine or bromine atom and one of $Q^1$, $Q^2$ and $Q^3$ may be a hydrogen atom. Furthermore, such silylating agents as hexa($C_{1-4}$)-alkylcyclotrisilazane, octa($C_{1-4}$)alkylcyclotetrasilazane, tri($C_{1-4}$)alkylsilylacetamide and bis-tri($C_{1-4}$)alkylsilylacetamide may also be used. As preferred examples of the silylating agent, there may be mentioned silyl compounds of the formula

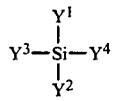

wherein $Y^1$ and $Y^2$ each is a lower alkyl, phenyl, benzyl or lower alkoxy group, $Y^3$ is t-butyl or isopropyl and $Y^4$ is a reactive group or atom capable of leaving the silylating agent. In the silylating agents represented by the above general formula, the lower alkyl group $Y^1$ and/or $Y^2$ is, for example, methyl, chloromethyl, ethyl, n-propyl, isopropyl, n-butyl or tert-butyl and the lower alkoxy group is, for example, methoxy, ethoxy, n-propoxy, isopropoxy, n-butoxy or t-butoxy. The reactive group or atom $Y^4$, which is capable of leaving the silylating agent, includes halogen atoms (e.g. chlorine, bromine), N-(trialkylsilyl)trifluoroacetimidoyloxy, N-(trialkylsilyl)acetimidoyloxy, acylamino groups (e.g. formylamino, acetylamino, propionylamino, butyrylamino, trifluoroacetylamino), (trialkylsilyl)amino groups [e.g. (tri-t-butyldimethylsilyl)amino, isopropyldimethylsilylamino, (chloromethyldimethylsilyl)amino], amino, alkylamino groups (e.g. methylamino, ethylamino, propylamino), N,N-dialkylamino groups (e.g. N,N-dimethylamino, N-chloromethyl-N-methylamino, N,N-diethylamino, N,N-dipropylamino, N-methyl-N-ethylamino, N-methyl-N-propylamino, N-ethyl-N-propylamino) and heterocyclic groups (e.g. imidazolyl), among others. The alkyl moiety in such reactive group or atom represented by $Y^4$ preferably contains 1–4 carbon atoms and is, for example, methyl, ethyl, n-propyl, isopropyl, n-butyl or t-butyl.

In concrete terms, examples of the silyl compound are N,O-bis(t-butyldimethylsilyl)trifluoroacetamide, N,O-bis(isopropyldimethylsilyl)acetamide, bis(dimethylisopropylsilyl)acetamide, isopropyldimethylsilylacetamide, bis(dimethyl-tert-butylsilyl)acetamide, N-methyl-N-t-butyldimethylsilylacetamide, N-methyl-N-isopropyldimethylsilyltrifluoroacetamide, N-t-butyldimethylsilyldiethylamine, 1,3-bis(chloromethyl)-1,1,3,3-tetra-t-butyldimethyldisilazane, N-isopropyldimethylsilylimidazole, t-butyldiphenylchlorosilane, isopropyldiethylchlorosilane, ispropylmethyldichlorsilane, tert-butyldimethylchlorosilne, isopropyldimethylchlorosilane and t-butyldiethylchlorosilane. When tert-butyldimethylchlorosilane or isopropyldimethylchlorosilane, for instance, is used, the silyl derivative can be isolated in a stable form. The silylation reaction is carried out at a temperature of 0°–50° C., preferably at a temperature up to 38° C., mostly at room temperature (about 20° C.), for several (about 10) minutes to 24 hours. It is convenient to carry out the reaction in a solvent inert to the reaction, such as, for example, ethyl acetate, dioxane, tetrahydrofuran, N,N-dimethylacetamide, N,N-dimethylformamide, dichloromethane, chloroform, benzene, toluene, acetone, methyl ethyl ketone or acetonitrile, or a mixture thereof. The reaction may be carried out in the presence of an inorganic base, such as sodium hydroxide, potassium hydroxide, sodium hydrogen carbonate, sodium carbonate or potassium carbonate, or an organic base, such as a trialkylamine (e.g. triethylamine, tributylamine), a triaralkylamine (e.g. tribenzylamine), such an organic tertiary amine as N-methylmorpholine, N-methylpiperidine, N,N-dialkylaniline, N,N-dialkylbenzylamine, pyridine, picoline or lutidine, or 1,5-diazabicyclo [4,3,0]non-5-ene, 1,4-diazabicyclo[2,2,2]octane or 1,8-diazabicyclo[5,4,4]undecene-7. When the base is liquid, it may be used also as the solvent. The thus-produced silyl derivative of compound [II] is used as the starting material in the step of reaction with a cyano compound, either in the form of a reaction mixture as it is or after isolation/purification by the conventional method such as described hereinbelow.

Among the thus-produced 1-silyl derivatives of compounds [II], those in which the above-mentioned $R^2$ is a protected amino group may be subjected to protective group elimination and then to acylation so as to give the 1-silyl derivatives of the desired compounds [II]. The acylation reaction at position 3 can easily be carried out by a simple procedure and give good yields, hence is very useful for the synthesis of various 2-oxoazetidinone derivatives each having the desired acyl group as the substituent. It is also possible to carry out the reaction with a cyano compound in a continuous manner directly following the acylation.

As the cyano compound, there may be used, for example, a compound of the formula

Z—CN wherein Z is an alkali or alkaline earth metal. To be concrete, there may be used, for example, potassium cyanide, sodium cyanide or calcium cyanide.

In this reaction, about 1-3 moles, preferably 1-1.1 moles, of the cyano compound is reacted with 1 mole of compound [II]. The reaction is generally carried out in a solvent. Usable solvents are water and common organic solvents, such as ethers (e.g. dioxane, tetrahydrofuran, diethyl ether), esters (e.g. ethyl acetate, ethyl formate), halogenated hydrocarbons (e.g. carbon tetrachloride, chloroform, dichloromethane), hydrocarbons (e.g. benzene, toluene, n-hexane), amides (e.g. dimethylformamide, dimethylacetamide), alcohols (e.g. methanol, ethanol, isopropanol, t-butanol), dimethyl sulfoxide, sulfolane and hexmethylphosphoramide, either alone or in admixture. Preferred among these are, for instance, water, dioxane, tetrahydrofuran, carbon tetrachloride, dichloromethane, chloroform, benzene, dimethylformamide, dimethylacetamide, methanol, isopropanol and dimethyl sulfoxide. When the reaction is carried out in the presence of a phase transfer catalyst, the production of those compounds [II] that have the CN group introduced thereinto in the configuration cis to $R^1$ is promoted and more favorable results are obtained. The term "phase transfer catalyst" as used herein means a substance capable of promoting the reaction by rendering one of two reactants separatedly present in two (liquid-liquid) phase soluble in the other liquid phase in the ion pair form. A phase transfer catalyst adequate for the achievement of the object of the reaction can be chosen, for instance, from among those which consist of, on one hand, a cation (ammonium or phosphonium ion) composed of a nitrogen or phosphorus atom and four groups bonded thereto and each selected from among alkyl, aryl and aralkyl groups and, on the other, an acid residue (anion, such as $Cl^-$, $Br^-$, $I^-$, $F^-$, $ClO_4^-$, $BF_4^-$, $BH_4^-$, $HSO_4^-$, $OH^-$ or $H_2PO_4^-$).

More specifically, there may be used, for instance, those consisting of halide ion and an ammonium ion having four substituents which are the same or different and each is selected from among alkyl, aryl and aralkyl groups, for example, tetraalkyl(total number of carbon atoms 4-50)ammonium halides such as tetramethylammonium chloride, tetraethylammonium chloride, tetra-n-butylammonium chloride, tri-n-octylmethyammonium chloride, trimethylstearylammonium chloride, tetra-n-amylammonium bromide and n-hexyltrimethylammonium bromide, aryltrialkyl(total number of carbon atoms 9-50)ammonium halides such as phenyltrimethylammonium bromide, and aralkyltrialkyl(total number of carbon atoms 13-50)ammonium halides such as benzyldimethyldecylammonium chloride, benzyltriethylammonium chloride and cetylbenzyldimethylammonium chloride; those consisting of $HSO_4^-$ (hydrogen sulfate ion) and an ammonium ion having four substituents which are the same or different and each is selected from among alkyl, aryl and aralkyl groups, for example, tetraalkyl(total number of carbon atoms 4-50-)ammonium hydrogen sulfates such as tetra-n-butylammonium hydrogen sulfate and tetramethylammonium hydrogen sulfate; those consisting of $OH^-$ (hydroxide ion) and an ammonium ion having four substituents which are the same or different and each is selected from among alkyl, aryl and aralkyl groups, for example, tetraalkyl(total number of carbon atoms 16-50)ammonium hydroxide such as tetra-n-butylammonium hydroxide; and those consisting of a halide ion and a phosphonium ion having four substituents which are the same or different and each is selected from among alkyl, aryl abd aralkyl groups, for example, tetraalkyl(total number of carbon atoms 4-50) phosphonium halides such as tetra-n-butylphosphonium bromide, aralkyltriaryl(total number of carbon atoms 9-50)phosphonium halides such as benzyltriphenylphosphonium chloride, and alkyltriaryl(total number of carbon atoms 19-50)phosphonium halides such as n-butyltriphenylphosphonium bromide. In particular, tri-n-octylmethylammoniun chloride, tetra-n-butylammonium hydrogen sulfate, tetra-n-amylammonium bromide, benzyltriethylammonium chloride and tetra-n-butylphosphonium bromide, among others, are used. These phase transfer catalysts are used in an amount of about 0.01-1 mole, preferably 0.05-0.2 mole, per mole of compound [II]. Where a phase transfer catalyst is used, a mixture of water and an organic solvent such as mentioned above is preferably used as the solvent. The mixing ratio is 0.5-5 parts, preferably 0.5-1 part, of the organic solvent per part of water. The reaction temperature is generally within the range of 0°-20° C. but not limited to this range. Adequate warming or cooling may be made as necessary. While the reaction time is to be adequately selected depending on the solvent, temperature and so forth, the reaction generally comes to an end in a short period of time.

After the reaction, the compound [I] produced can be recovered in any desired purity by a per se known isolation/purification method, such as solvent extraction, recrystallization or chromatography, although the reaction mixture as it is may also be used as the starting material in the next reaction step.

When the thus-obtained compound [I] has a protective group, the protective group may be eliminated as necessary. The method of eliminating the protective group can adequately be selected, depending on the nature of the protective group, from the conventional methods, such as the method using an acid, the method using a base, the method involving reduction, and the method using thiourea or sodium N-methyldithiocarbamate. In the method using an acid, the acid, which should be selected depending on the kind of the protective group and other factors, is, for example, such an inorganic acid as hydrochloric, sulfuric or phosphoric acid, such an organic acid as formic, acetic, trifluoroacetic, propionic, benzenesulfonic or p-toluenesulfonic acid, or an acidic ion exchange resin. In the method using a base, the base, which is to be selected depending on the kind of the protective group and other conditions, is, for example, such an inorganic base as an alkali metal (e.g. sodium, potassium) or alkaline earth metal (e.g. calcium, magnesium) hydroxide or carbonate, a metal alkoxide, such an organic base as an organic amine or a quaternary ammonium salt, or a basic ion exchange resin. When a solvent is used in conducting the above method using an acid or base, the solvent is mostly a hydrophilic organic solvent, water, or a mixture of these. In the method involving reduction, the method of reduction, though depending on the protective group species and other conditions, is, for example, the method using a metal (e.g. tin, zinc) or a metal compound (e.g. chromiun dichloride, chromium acetate) in combination with an organic or inorganic acid (e.g. propionic acid, hydrochloric acid), or the method involving reduction in the presence of a metal catalyst for catalytic reduction. The catalyst to be used in said catalytic reduction includes, among others, platinum catalysts such as platinum wire, platinum sponge, platinum black, platinum oxide and colloidal platinum, palladium catalysts such as palladium sponge, palladium black, palladium oxide, palladium-on-barium oxide, palladium-on-barium carbonate, palladium-on-carbon, palladium-on-silica gel and colloidal palladium, and reduced nickel, nickel oxide, Raney nickel and Urushibara nickel. In the reduction method using a metal and an acid, such a metal compound as iron or chromium and such an inorganic acid as hydrochloric acid or such an organic acid as formic, acetic or propionic acid are used. The method involving reduction is generally carried out in a solvent. Thus, for example, in the catalytic reduction, such alcohols as methanol, ethanol, propyl alcohol and isopropyl alcohol, and ethyl acetate, among others, are used frequently. In the method using a metal and an acid, water and acetone, among other, are frequently used and, when the acid is liquid, the acid itself can be used also as the solvent. The reaction is generally carried out with or without cooling or warming. The thus-produced compound [II] can be isolated and purified by a known method such as mentioned above although the reaction mixture itself can be used as the starting material in the next reaction step.

When $R^2$ in the thus-obtained compound [I] is an amino group, the compound [I] may optionally be acylated by reaction with a carboxylic acid of the formula

R°COOH    [IV]

wherein R°CO is such an acyl group as mentioned for $R^1$, $R^2$ and $R^4$, or a functional derivative thereof.

The compound [I] in which $R^2$ is an amino group may be used in the free form or in the form of a salt, ester or silyl derivative such as mentioned for the compound [II]. The functional derivative of the carboxylic acid [IV] is, for example, an acid halide, acid anhydride, active amide or active ester. Examples of such functional derivative of the organic acid are as follows:

(1) Acid anhydrides

The acid anhydrides include, among others, mixed acid anhydrides with hydrogen halides (e.g. hydrogen chloride, hydrogen bromide), mixed acid anhydrides with monoalkyl carbonates, mixed acid anhydrides with aliphatic carboxylic acids (e.g. acetic acid, pivalic acid, valeric acid, isopentanoic acid, trichloroacetic acid), mixed acid anhydrides with aromatic carboxylic acids (e.g. benzoic acid), and symmetric acid anhydrides.

(2) Active amides

The active amides include, among others, amides with imidazole, 4-substituted imidazoles, dimethylpyrazole and benzotriazole.

(3) Active esters

The active esters include, among others, methyl, ethyl, methoxymethyl, propargyl, 4-nitrophenyl, 2,4-dinitrophenyl, trichlorophenyl, pentachlorophenyl and mesylphenyl esters and further esters of such carboxylic acids as mentioned above with 1-hydroxy-1H-2-pyridone, N-hydroxysuccinimide, N-hydroxy-5-norbornene-2,3-dicarboximide and N-hydroxyphthalimide.

An adequate functional derivative of the organic acid can be selected from among those mentioned above depending on the kind of acid to be used. Furthermore, when an acid in the free form is used as the acylating agent, the reaction is preferably carried out in the presence of a condensing agent. The condensing agent is, for example, N,N'-dicyclohexylcarbodiimide, N-cyclohexyl-N'-morpholinoethylcarbodiimide, N-cyclohexyl-N'-(4-diethylaminocyclohexyl)carbodiimide or N-ethyl-N'-(3-dimethylaminopropyl)carbodiimide.

Said acylation reaction is generally carried out in a solvent. Usable solvents are water, acetone, dioxane, acetonitrile, methylene chloride, chloroform, dichloroethane, tetrahydrofuran, ethyl acetate, dimethylformamide, pyridine and other common organic solvents inert to the reaction. Hydrophilic solvents may be used in admixture with water.

Furthermore, the acylation reaction may be carried out in the presence of such an inorganic base as sodium hydroxide, sodium carbonate, potassium carbonate or sodium hydrogen carbonate, or such an organic base as trimethylamine, triethylamine, tributylamine, N-methylmorpholine, N-methylpiperidine, a like trialkylamine, N,N-dialkylaniline, N,N-dialkylbenzylamine, pyridine, picoline, lutidine, a like organic tertiaty amine, 1,5-diazabicyclo[4,3,0]non-5-ene, 1,4-diazabicyclo[2,2,2]octane or 1,8-diazabicyclo[5,4,4]undecene-7. The base or the above-mentioned condensing agent, if liquid, may be used also as the solvent. The reaction temperature is not critical, but in most cases the reaction is generally carried out under cooling or at room temperature.

Furthermore, when the compound [I] and/or the acylating agent [II] contains an asymmetric carbon atom or atoms, the acylation may be carried out using the reactant either in the form of stereoisomer or in the form of a mixture of stereoisomers. If the reaction leads to formation of a mixture of stereoisomers, the isomers can respectively be isolated as necessary by a conventional method such as chromatography or recrystallization. When the thus-obtained compound [I] (where $R^2 \neq NH_2$) has a protective group, said group can be eliminated as necessary in the same manner as mentioned above. Furthermore, the compound [I] obtained in the above manner in which W is a hydrogen atom may also be sulfonated.

The sulfonation just mentioned above refers to the introduction of a sulfo group into the compound [I] (where W=H) at the 1-position and is carried out, for instance, by reacting the compound [I] (where W=H) with sulfur trioxide or a reactive derivative of sulfur trioxide, among others. The compound [I] (where W=H) is used in the free form or in the form of a salt, ester or silyl derivative such as mentioned for the compound [II], and may be subjected to the reaction either in the form of a theoretically possible individual stereoisomer or in the form of a mixture of stereoisomers. The reactive derivative of sulfur trioxide includes, among others, such adducts as sulfur trioxide-base complexes (e.g. sulfur trioxide-pyridine, sulfur trioxide-trimethylamine, sulfur trioxide-picoline, sulfur trioxide-lutidine, sulfur trioxide-N,N-dimethylformamide), sulfur trioxide-dioxane and sulfur trioxidechlorosulfonic acid.

The above sulfonation reaction is carried out using about 1–10 moles, preferably about 1–5 moles, of sulfur trioxide or a reactive derivative thereof per mole of compound [I] (where W=H). The reaction temperature is about $-78°$ to about 80° C., preferably about $-20°$ to about 60° C. The reaction may be carried out in a solvent. Usable solvents include water and common organic solvents, for example, such ethers as dioxane, tetrahydrofuran and diethyl ether, such esters as ethyl acetate and ethyl formate, such halogenated hydrocarbons as chloroform and dichloromethane, such hydrocarbons as benzene, toluene and n-hexane, and such amides as N,N-dimethylformamide and N,N-dimethylacetamide. Such solvents are used each alone or in admixture. The reaction is generally complete in several tens of minutes to scores of hours, in some cases in scores of days, depending on the starting compound [I] (where W=H), sulfonating agent, reaction temperature and solvent. After the reaction, the reaction mixture is subjected to a per se known purification/isolation procedure, such as solvent extraction, recrystallization or chromatography, to give the compound [I] (where=-$SO_3H$) in any desired purity. When there is a protective group, said group may be eliminated by a method such as mentioned above.

The thus-obtained compound [I], when in the free form, may be converted to a salt or ester such as mentioned for the compound [II] by a conventional method. Conversely, when the compound [I] is obtained in the salt or ester form, the salt or ester may be converted to the free form by a conventional method.

The thus-obtained 4-cyano-2-azetidinone derivatives [I] are novel compounds and can be used widely as advantageous intermediates for the synthesis of various 4-substituted-2-azetidinone derivatives. Moreover, those compounds where $W=SO_3H$ have antimicrobial and beta-lactamase inhibiting activities.

Compounds [III] are produced, for example, by subjecting a compound [I] (W=H) to hydration, followed by protective group elimination as necessary. This hydration reaction converts the cyano group in the compound [I] (W=H) into a carbamoyl group. The starting compound [I] (W=H) may be in the free form or in the salt, ester or silyl derivative form such as mentioned for the compound [II]. For the compound [I] (W=H) which has substituents at the 3- and 4-positions, there occurs cis-trans isomerism and moreover the carbon atoms in the 3- and 4-positions are asymmetric. As a result, there can theoretically exist a total of at least four stereoisomers for each compound [I]. These stereoisomers may be used either each alone or in the form of a mixture. The same may be said of the case where the group $R^1$ contains an asymmetric carbon atom or atoms, and the resulting stereoisomers also may be used either each alone or in the form of a mixture.

The hydration reaction is carried out by any method by which the cyano group in position 4 of the compound [I] (W=H) is converted to a carbamoyl group, for example, the method comprising reacting the compound [I] (W=H) with an acid or base, or the method comprising reacting the compound [I] (W=H) with hydrogen peroxide in the presence of a base. Examples of said base are alkali metal (e.g. lithium, potassium, sodium) or alkaline earch metal (e.g. calcium, magnesium) hydroxides (e.g. potassium hydroxide, sodium hydroxide, lithium hydroxide, calcium hydroxide, magnesium hydroxide) and carbonates (e.g. sodium carbonate, potassium carbonate, calcium carbonate), like inorganic bases, metal alkoxides (e.g. sodium methylate, sodium ethylate), organic amines (e.g. triethylamine, N,N-dimethylaniline, diisopropylamine), quaternary ammonium salts (e.g. tetra-n-butylammonium hydroxide), like organic bases, and basic ion exchange resins. Among them, alkali metal hydroxides (e.g. sodium hydroxide) are frequently used as preferred bases. The acid includes, among others, such inorganic acids and salts as hydrochloric acid, sulfuric acid, phosphoric acid, polyphosphoric acid, ferric chloride, zinc chloride, manganese dioxide, boron trifluoride, palladium chloride and titanium tetrachloride, such organic acids as formic acid, acetic acid, p-toluenesulfonic acid and trifluoroacetic acid, silica gel and acidic ion exchange resins. Especially preferred among them are such acids as hydrochloric acid, sulfuric acids, manganese dioxide, palladium chloride and titanium tetrachloride. These acids or bases are used generally in an amount of 0.1–4.0 moles, preferably 0.1–1.0 mole, per mole of compound [I] (W=H). When hydrogen peroxide is used, the bases are used in an amount of 0.05–4.0 moles, preferably 0.05–1.0 mole, per mole of compound [I] (W=H). Hydrogen peroxide is used in an amount of 1.0–10 moles, preferably 1.0–4 moles, per mole of compound [I] (W=H). This reaction is generally carried out in a solvent. Usable solvents are, for instance, water, ethers (e.g. tetrahydrofuran, dioxane), acid amides (e.g. N,N-dimethylformamide, N,N-dimethylacetamide), hydrocarbons (e.g. benzene), ketones (e.g. acetone), alcohols (e.g. methanol, ethanol, propanol, butanol), halogenated hydrocarbons (e.g. chloroform, dichloromethane), fatty acids (e.g. formic acid, acetic acid), esters (e.g. ethyl acetate), dimethyl sulfoxide, sulfolane and hexamethylphosphoramide, and mixtures of these. Among these, frequently used are water, isopropanol, tetrahydrofuran, dichloromethane, dimethyl sulfoxide and the like. When a mixture of water and an organic solvent is used as the solvent, the reaction may be carried out in the presence of a phase transfer catalyst. The phase transfer catalyst may be the one as mentioned hereinbefore in connection with the reaction of a compound [II] and a cyano compound. The phase transfer catalyst is used in an amount of about 0.1–2 moles, preferably 0.5–1 mole, per mole of compound [I] (W=H). The reaction temperature is generally selected within the range of 0°–80° C. but is not limited thereto. Thus, the reaction may be conducted with adequate warming or cooling as necessary. The reaction is complete generally in a short period of time.

After the reaction, the reaction mixture is subjected to a per se known purification/isolation procedure, such as solvent extraction, recrystallization or chromatography, to give a compound [III] in any desired purity. The reaction mixture as it is may also be used as the starting material in the next reaction step. When this reaction leads to formation of isomers, the respective isomers may be isolated as necessary by a conventional method, and, when the substituent of the compound [III] has a protective group, said group may be eliminated as necessary in the same manner as mentioned above.

The thus-obtained compound [III] can evidently be sulfonated in the same manner as the sulfonation of compound [I] (where W=H), to give the corresponding compound [III] where has a sulfo group at 1-position.

When the thus-produced compound [III] is in the free form, it may be converted to a salt or ester such as mentioned above by a conventional method. When the compound [III] is obtained in the salt or ester form, it may be converted to the free form by a conventional method.

The compounds [III] which have $SO_3H$ at 1-position are novel compounds and have excellent antibacterial and betalactamase inhibiting activities.

The compounds [III] and the salts or esters thereof are valuable antibiotics, which are active against a variety of gram-positive or gram-negative bacteria; they are used as medicine in humans and domestic animals and are applied as safe antimicrobial agents for the treatment of infections caused by gram-positive or gram-negative bacteria. Furthermore, the antimicrobial agents are added to animal feed as disinfectants for preservation of feedstuffs. The antibiotics can also be used in the form of an aqueous formulation at a concentration in the range of 0.1 to 100 ppm (i.e., 0.1 to 100 parts of antibiotic per 1,000,000 parts of solution) as antimicrobial preparations for the destroying and inhibiting the growth of harmful bacteria, for example, in equipment and instruments used in medical or dental treatment, or else for preventing the growth of harmful bacteria in an industrial aqueous medium, for example, in water-based paints or in waste water from paper mills.

The compoubnds [III] can be employed alone or in combination with one or more active components in the form of all the different types of pharmaceutical preparations such as capsules, tablets and powders, as well as solutions, suspensions, and elixirs. These preparations can be administered orally, intravenously, or intramuscularly.

The tablets for oral administration may contain common inert ingredients, such as, for example, a binding agent, e.g., syrup, gum arabic, gelatin, sorbitol, gum tragacanth, or polyvinylpyrrolidone, a filler, e.g., lactose or others sugars, corn starch, calcium phosphate, sorbitol, or glycine, a lubricant, e.g., magnesium stearate, talcum, polyethylene glycol, or silicon dioxide, a decomposition-promoting agent, e.g., potato starch, or a suitable wetting agent such as sodium lauryl sulfate.

The tablets can be provided with coatings using technologically known processes.

The liquid preparations for oral administration can exist in such forms of administration as suspensions in water or oil, solutions, emulsions, syrups, elixirs, etc.; but they can also be produced as lyophilized preparations, which can be dissolved at any time as needed in water or a suitable solvent. These liquid preparations can contain a suspending agent, e.g., sorbitol syrup, methylcellulose, glucose/syrup, gelatin, hydroxyethylcellulose, carboxymethylcellulose, or aluminum stearate gel, a solidified edible oil, e.g., almond oil, coconut oil fractions, oleaginous esters, propylene glycol, or ethyl alcohol, or a preservative, e.g., methyl or propyl p-hydroxybenzoate, or sorbit acid. Suppositories may contain typical suppository bases, e.g., theobroma oil or other glycerides.

Injectable preparations can be provided in ampules or other contains for a dosage unit with addition of a preservative. These compositions can exist in such dosage forms as suspensions, solutions, or emulsions in an aqueous or oily carrier, and can contain one or more suitable pharmacological aids, said, a suspending agent, a stabilizer and/or a dispersing agent. Alternatively, the compound may also be provided in powder form, from which the preparation to be administered is reconstituted just before use with a suitable solvent, say, with sterilized, pyrogen-free water.

The compound can also be formulated in suitable dosage forms, such that it can be absorbed through the nasal and pharyngeal mucosa or bronchial tissue, for example, powder, liquid agents for spraying or inhalation, lozenges, preparations for painting the throat, etc. For opthalmologic or otologic use, the compounds can be administered as liquid-containing or semisolid capsules or as drops designated for drop administration. Furthermore, they can be formulated with hydrophobic or hydrophilic pharmaceutical bases in such forms of administration as ointments, creams, lotions, preparations for painting, powders, etc., so as to make the preparations available for external use.

In addition to carriers, these preparations may contain other components such as stabilizers, binding agents, antioxidation agents, preservatives, lubricating agents, suspending agents, flow-property modifying agents, or flavoring agents. Furthermore, one or more additional compounds can be incorporated into the compositions, so that a broader antimicrobial spectrum is achieved.

For administration to domestic animals, the compound of the present invention can be formulated in combination with agents that release it only after a certain time, so that intramammarily active preparations are also obtainable.

The compounds [III] can be administered to mammals as therapeutic agents against microbial infections, for example, to treat respiratory-tract infections, urinary-tract infections, purulent infections, bile-duct infections, intestinal infections, gyneologic infections, surgical infections, etc. The daily dose is variable, depending on the condition of the patient to be treated, the patient's weight, the mode and frequency of administration, as well as the special parenteral procedures generally suitable for infections, or the oral procedure used for intestinal infections. In general, the daily oral dose contains the compound in an amount of, say, 15 to 600 mg/kg of the patient's body weight; they are used in one or several dosages. The daily dose appropriate for administration to an adult human is about 10 to about 200 mg/kg of the compound in relation to the body weight and which is preferably given non-orally in the form of 2 to 4 doses of 2.5 to 100 mg/kg each parenterally.

A pharmaceutical formulation containing compound [III] can, for example, be administered in various solid or liquid, oral dosage units. The liquid or solid formulation may contain 0.5 to 99% of the compound. The preferable concentration range for the substance extends from about 10% to about 60%. The formulation generally contains about 15 mg to 1500 mg of the compound in each dosage unit, and it is generally preferred to use a dosage unit in the range of about 250 mg to 1000 mg of the compound.

In addition to the uses indicated in the foregoing, compounds [III] can be used in combination with beta-lactam antibiotics, since they possess beta-lactam-inhibiting activity. Examples of such beta-lactam antibiotics include penicillin antibiotics such as benzyl penicillin, phenoxymethyl penicillin, carbenicillin, ampicillin, amoxicillin, sulbenicillin, etc., cephalosporin antibiotics such as cephaloridine, cephalothin, cefazolin, cephalexin, cefoxitin, cephacetrile, cefamandole, cefmenoxime, cefsulodin, cefotiam, cefotaxime, cephapirin, ceftizoxime, cefradin, cephaloglycin, and the like.

Experimental Testing

The following tabular data refer to the minimal inhibitory concentration (MIC) of some typical compounds [III].

Method

The minimum inhibitory concentrations of the tested compounds were determined by the agar-dilution method. Then, in each case 1.0 ml of an aqueous solution, obtained in serial dilutions of the tested compounds, was poured in a test petri dish. Next, 9.0 ml of trypticase soy agar was poured in, and the liquids were mixed. A full loop of a bacterial suspension (about $10^8$ CFU/ml) of the particular test organism was spread on the mixed-agar plate. In each case, after incubation overnight at 37° C., the lowest concentration of the compounds, which to all appearances produced total inhibition of growth of the test microorganism, was evaluated as the minimum inhibitory concentration.

| Test Microorganisms: | | |
|---|---|---|
| (1) *Enterobacter cloacae* IFO 12937 | | |
| (2) *Klebsiella pneumoniae* TN 1711 | | |
| Result: | | |
| | (μg/ml) Microorganism | |
| Compound | (1) | (2) |
| Cis-3-[2-(2-amino-4-thiazolyl)-2-(1-methyl-1-carboxyethyloxyimino)acetamido]-4-carbamoyl-2-oxoazetidine-1-sulfonic acid (syn-isomer) | 1.56 | 0.39 |
| trans-3-[2-(2-amino-4-thiazolyl)-2-(1-methyl-1-carboxyethyloxyimino)acetamido]-4-carbamoyl-2-oxoazetidin-1-sulfonic acid (syn-isomer) | 6.25 | 3.13 |

Furthermore, the compound [I], when reacted with hydrogen sulfide, gives a compound having a —CSNH$_2$ group in place of the cyano group at the 4-position of compound [I]. This reaction is preferably carried out using about 1.0–3 moles of hydrogen sulfide per mole of compound [I] or salt, ester or silyl derivative thereof. The reaction is advantageously conducted at or below room temperature, preferably in a solvent such as, for example, chloroform, dichloromethane, benzene, ethyl acetate, tetrahydrofuran, dioxane, N,N-dimethylformamide, N,N-dimethylacetamide, dimethyl sulfoxide, acetic acid or water. Generally, the reaction is complete in a short period of time.

Furthermore, the reaction of the compound [I] with an alcohol such as methanol or ethanol gives a compound having an alkoxycarbonyl group in place of the cyano group at the position 4 of compound [I]. In that reaction, an at least equimolar amount of alcohol to the compound [I] is used and in many cases the alcohol itself is used as the solvent. When a solvent is used, the solvent is preferably selected from among such solvents as chloroform, dichloromethane, benzene, tetrahydrofuran, dioxane, N,N-dimethylformamide, N,N-dimethylacetamide and dimethyl sulfoxide. The reaction temperature is generally within the range of 0°–80° C., but not limited to this condition. Thus, the reaction may be carried out with adequate warming or cooling as necessary. The reaction time and other conditions depend on the solvent and temperature employed, among others. Copresence of such an inorganic acid as sulfuric, hydrochloric or phosphoric acid, such an organic acid as acetic or p-toluenesulfonic acid or such a Lewis acid as aluminum chloride, zinc chloride or boron trifluoride may result in a reduced reaction time.

The starting compounds [II] to be used in accordance with the invention can be prepared, for example, by the process mentioned hereinbelow. Thus, the starting compounds [II] can be prepared, for example, by the method described in Tetrahedron Letters, 4059 (1978) or OLS No. 2839646 or a modification thereof, or by the method described, for example, in Annalen der Chemie, 1974, 539. These synthetic methods can be illustrated in the following by routes (1) and (2).

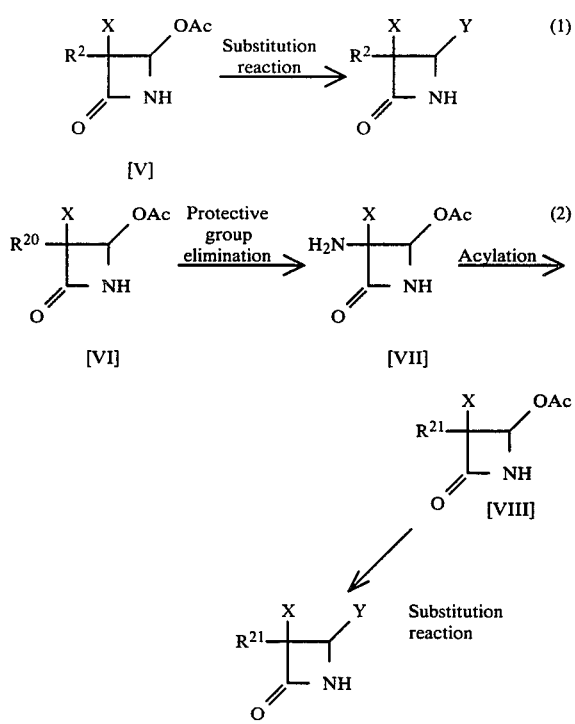

In each of the above formulas, $R^2$, Y and X are as defined above, $R^{20}$ is a protected amino group awnd $R^{21}$ is an acylated amino group.

The following examples and reference examples illustrate the present invention in more detail. The NMR spectra were recorded on a Varian model HA 100 (100 MHz) with tetramethylsilane as a standard, and the δ values are given in ppm. The abbreviation s stands for singlet, br. s. for broad singlet, d for doublet, dd for double doublet, t for triplet, q for quartet, m for multiplet, ABq for AB-pattern quartet, J for coupling constant, THF for tetrahydrofuran, DMF for dimethylformamide, DMSO for dimethyl sulfoxide, br. or broad for broad, and arom for aromatic.

In the following examples and reference examples, the silica gel column chromatography was performed, unless otherwise stated, using Art. 9385, 230–400 mesh, Kiesel Gel 60 (Merck) and those fractions which, in TLC analysis, gave a spot having the same $R_f$ value as that for the main spot as found newly upon TLC analysis of the crude product before chromatographic purification were collected. The TLC was carried out, unless otherwise stated, using Art. 5642 HPTLC Kiesel Gel 60 $F_{254}$ (Merck) plates and the same developing solvent as used in the column chromatography, with a UV detector. The XAD-II (100–200 mesh) column chromatography was performed using water-to-20% aqueous ethanol as the developing solvent system, and the fractions showing an absorption at 254 nm (as measured with a Swedish LKB CORD 2) were collected and lyophilized to give a purified product.

BEST MODE FOR WORKING THE INVENTION

EXAMPLE 1

In 2 ml of dimethylformamide was dissolved 0.488 g of (3S, 4S)-4-cyano-3-[D-2-(4-2-(4-ethyl-2,3,-dioxo-2,3-dioxo-1-piperazinecarboxamido)-2-(thiophen-2-yl)]acetamido-2-azetidinone. To the solution was added at −70° C. 3.5 ml of dimethylformamide containing 0.536 g of a complex of sulfuric anhydride and dimethylformamide, and the reaction was allowed to proceed at 0° C. for two days. The reaction solution, to which was added 0.5 ml of pyridine, was subjected to concentration under reduced pressure. To the residue was added water, and insolubles were removed by filtration. The filtrate was allowed to pass through a column of Dowex 50 Na-type (manufactured by Dow-Chemical, Co.), which was purified by means of a column of Amberlite XAD-II (manufactured by Rohm & Haas, Co.) to yield 0.350 g of sodium (3S, 4S)-4-cyano-3-[D-2-(4-ethyl-2,3-dioxo-1-piperazinecarboxamido)-2-(thiophen-2-yl]-acetamido-2-azetidinone-1-sulfonate.

IR$\nu_{max}^{KBr}$cm$^{-1}$: 1780, 1710, 1675, 1510, 1280, 1260, 1050.

NMR(DMSO-d$_6$, ppm): 1.10 (t, J=5 Hz, CH$_3$), 3.41 (q, J=5 Hz, —CH$_2$—), 3.60 (m, —CH$_2$—), 3.93 (m, —CH$_2$—), 4.90 (d, J=4 Hz, C$_4$—H), 5.30 (dd, J=4, 8 Hz, C$_3$—H), 5.38 (d, J=4 Hz,

6.90–7.60 (m, aromH), 9.76 (d, J=4 Hz, NH), 9.83 (d, J=8 Hz, NH)

EXAMPLE 2

(1) In 2 ml of DMF was dissolved 0.220 g of (3S, 4S)-3-[2-(2-chloroacetamidothiazol-4-yl)-2-methoxyimino]acetamido-4-cyano-2-azetidinone. To the solution was added at −70° C. 1.8 ml of a DMF solution containing 0.275 g of a complex of sulfuric anhydride and DMF, and the reaction was allowed to proceed at 0° C. for three days. The reaction solution, to which was added 0.5 ml of pyridine, was treated in a manner analogous to that of Example 1 to yield 0.170 g of sodium (3S, 4S)-3-[2-(2-chloroacetamidothiazol-4-yl)-2-methoxyimino]acetamido-4-cyano-2-azetidinone-1-sulfonate.

IR$\nu_{max}^{KBr}$cm$^{-1}$: 1780, 1670, 1540, 1260, 1055.

NMR(D$_2$O, external standard, ppm): 4.04 (s, OCH$_3$), 4.44 (s, —CH$_2$—), 5.26 (d, J=5 Hz, C$_4$—H), 5.46 (d, J=5 Hz, C$_3$—H), 7.50

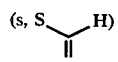

(2) In 6 ml of water was dissolved 0.150 g of the chloroacetamido compound. To the solution was added under ice-cooling 0.050 g of sodium monomethyldithiocarbamate, and the mixture was stirred at room temperature (about 25° C.) for three hours. The reaction solution was purified on a column of XAD-II to yield 0.067 g of sodium (3S, 4S)-3-[2-(2-aminothiazol-4-yl]-2-methoxyimino]acetamido-4-cyano-2-azetidinone-1-sulfonate.

IR$\nu_{max}^{KBr}$cm$^{-1}$: 1780, 1665, 1610, 1520, 1260, 1050.

NMR(D$_2$O, external standard, ppm): 4.00 (s, OCH$_3$), 5.24 (d, J=5 Hz, C$_4$—H), 5.45 (d, J=5 Hz, C$_3$—H), 7.06

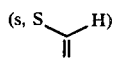

EXAMPLE 3

(1) In 2 ml of DMF was dissolved 0.482 g of (3S, 4R)-3-[2-(2-chloroacetamidothiazol-4-yl)-2-methoxyimino]acetamido-4-cyano-2-azetidinone. To the solution was added at −70° C. 3.9 ml of DMF solution containng 0.597 g of a complex of sulfuric anhydride and DMF, and the reaction is allowed to proceed at 0° C. for two days. The reaction solution, to which was added 0.5 ml of pyridine, was treated in a manner similar to that of Example 1 to yield 0.390 g of sodium (3S, 4R)-3-[2-(2-chloroacetamidothiazol-4-yl)-2-methoxyimino]-acetamido-4-cyano-2-azetidinone-1-sulfonate.

IR$\nu_{max}^{KBr}$cm$^{-1}$: 1785, 1670, 1550, 1260, 1055.

NMR(D$_2$O, external standard, ppm): 4.06 (s, OCH$_3$), 4.44 (s, —CH$_2$—), 5.14 (d, J=2 Hz, C$_4$—H), 5.40 (d, J=2 Hz, C$_3$—H), 7.43

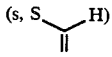

(2) In 6 ml of water was dissolved 0.190 g of the chloroacetamido compound. The solution was treated in a manner similar to that of Reference Example 2, 2) while using 0.052 g of sodium monomethyldithiocarbamate to thereby yield 0.074 g of sodium (3S, 4R)-3-[2-(2- aminothiazol-4-yl)-2-methoxyimino]acetamido-2-azetidinone-1-sulfonte.

IR$\nu_{max}^{KBr}$cm$^{-1}$: 1780, 1660, 1615, 1520, 1280, 1250, 1050.

NMR(D$_2$O, external standard, ppm): 4.02 (s, OCH$_3$), 5.12 (d, J=3 Hz, C$_4$—H), 5.37 (d, J=3 Hz, C$_3$—H), 6.96

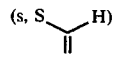

EXAMPLE 4

To a mixture of 1.196 g of D-2-(4-ethyl-2,3-dioxo-1-piperazinocarboxamido)-2-(thiophen-2-yl)acetate, 20 ml of methylene chloride and 0.530 g of triethylamine was added 0.775 g of pulverized phosphorus pentachloride with stirring under ice-cooling. The mixture was stirred for one hour under ice-cooling, which was concentrated under reduced pressure. To the concentrate was washed by several times of decantation by the addition of n-hexane. To the residue was added dry tetrahydrofuran to remove the insolubles.

On the other hand, 0.992 g of p-toluenesulfonate of (3S, 4S)-3-amino-4-cyano-2-azetidinone was dissolved in 15 ml of dry tetrahydrofuran. To the solution was added under ice-cooling 1.060 g of triethylamine, to which was further added the tetrahydrofuran solution of acid chloride prepared as above. The mixture was stirred at room temperature (about 25° C.) for 40 minutes, which was concentrated under reduced pressure. The concentrate was subjected to a silica- gel column chromatography[developer, ethyl acetate:chloroform:methanol (3:3:1)]to yield 0.560 g of (3S, 4S)-4-cyano-3-[D-2-(4-ethyl-2,3-dioxo-1-piperazinocarboxamido)-2-(thiophen-2-yl]acetamido-2-azetidinone IR$\nu_{max}^{KBr}$cm$^{-1}$: 1785, 1710, 1670, 1500.

NMR(DMSO-d$_6$, ppm): 1.09 (t, J=5 Hz, CH$_3$), 3.40 (q, J=5 Hz, —CH$_2$—, 3.56 (m, —CH$_2$—), 3.90 (m, —CH$_2$—), 4.76 (d, J=4 Hz, C$_4$—H), 5.30 (dd, J=8, 4 Hz, C$_3$—H), 5.38 (d, J=4 Hz,

—CH—),
|

6.90–7.60 (m, arom H), 9.03 (br. s. NH), 9.70 (d, J=4 Hz, NH), 9.80 (d, J=8 Hz, NH)

EXAMPLE 5

In 15 ml of dry tetrahydrofuan was suspended 0.960 g of p-toluenesulfonate of (3S, 4S)-3-amino-4-cyano-2-azetidinone. To the suspension were added under ice-cooling 1.400 g of triethylamine, to which was added 10 ml of dry tetrahydrofuran in which was dissolved 2-(2-chloroacetamidothiazol-4-yl)-2-methoxyiminoacetyl chloride hydrochloride. The mixture was stirred at room temperature (about 25° C.) for 30 minutes. The reaction solution was concentrated under reduced pressure. The concentrate was subjected to a silica-gel column chromatography [developer, ethy acetate:chloroform:methanol (3:3:1)] to yield 0.910 g of (3S, 4S)-3-[2-(2-chloroacetamidothiazol-4-yl)-2-methoxyimino]acetamido-4-cyano-2-azetidinone.

IR$\nu_{max}^{KBr}$cm$^{-1}$: 1790, 1675, 1540 1050.

NMR(DMSO+D$_2$O, ppm): 3.93 (s, OCH$_3$), 4.33 (s, —CH$_2$—), 4.83 (d, J=4 Hz, C$_4$—H). 5.40 (d, J=4 Hz) C$_3$—H), 7.46

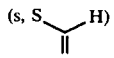

EXAMPLE 6

In 10 ml of dry tetrahydrofuran was suspended 0.540 g of p-toluenesulfonate of (3S, 4R)-3-amino-4-cyano-2-azetidinone. To the suspension were added under ice-cooling 0.787 g of triethylamine, to which was added 5 ml of dry Tetrahydrofuran in which was dissolved 0.600 g of 2-(2-chloracetamidothiazol-4-yl)-2-methoxyiminoacetyl chloride hydrochloride. The mixture was stirred at room temperature (about 25° C.) for 30 minutes. The reaction solution was subjected to a silicagel column chromatography [developer, ethyl acetate:chloroform:methanol (3:3:1)] to yield 0.525 g of (3S, 4R)-4-cyano-3-[2-(2-chloroacetamidothiazol)-4-yl)-2-methoxyimino]acetamido-2-azetidinone.

IR$\nu_{max}^{KBr}$cm$^{-1}$: 1780, 1670, 1540, 1040.

NMR(DMSO-d$_6$, ppm) 3.92 (s, OCH$_3$), 4.36 (s, —CH$_2$—), —CH$_2$—), 4.53 (d, J=2 Hz, C$_4$—H), 5.23 (dd, J=2, 5 Hz, C$_3$—H), 7.50

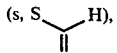

9.10 (s, NH), 9.56 (d, J=5 Hz, NH).

EXAMPLE 7

In 100 ml of methylene chloride were dissolved under ice-cooling 5 g of p-toluenesulfonate of (3S, 4RS)-3-amino-4-cyano-2-azetidinone and 4.2 g of pyridine. To the solution was added 3 g of phenylacetyl chloride. The mixture was stirred at room temperature (about 25° C.) for ten minutes, which was shaken with water. The organic layer was separated and dried on anhydrous magnesium sulfate, then concentrated under reduced pressure. The concentrate was purified on a silicagel column chromatography [ethyl acetate:n-hexane (2:1)] to yield 1.16 g of (3S, 4S)-4-cyano-3-phenylacetamido-2-azetidinone (A) and subsequently 0.84 g of a corresponding (3S, 4R)-derivative (B).

(A):

IR$\nu_{max}^{KBr}$cm$^{-1}$: 2250, 1770, 1665, 1530, 1350.

NMR(DMSO-d$_6$, ppm): 3.60 (s, —CH$_2$—), 4.20 (d, J=4 Hz, C$_4$—H), 4.86 (dd, J=4, 8 Hz, C$_3$—H), 6.56 (d, J=8 Hz, NH), 7.26 (s, arom H).

(B):

IR$\nu_{max}^{KBr}$cm$^{-1}$: 2250, 1780, 1660, 1520, 1350.

NMR(DMSO-d$_6$, ppm): 3.60 (s, —CH$_2$—), 4.10 (d, J=2 Hz, C$_4$H), 4.80 (dd, J=2, 8 Hz, C$_3$—H), 6.60 (d, J=8 Hz, NH), 7.20 (s, arom H).

EXAMPLE 8

A mixture of 1.66 g of p-toluenesulfonate of (3S, 4R)-3-amino-4-cyano-2-azetidinone, 0.5 g of pyridine and 5 ml of methylene chloride was stirred at room temperature for 15 minutes. To the mixture, while stirring under ice-cooling, were added 10 ml of propylene oxide and subsequently 1.1 g of 2-trimethylsilylethoxycarbonylchloride, followed by stirring at room temperature for 30 minutes. The reaction solution was concentrated under reduced pressure, and the concentrate was subjected to a silicagel column chromatography [developer, ethyl acetate:n-hexane (1:1)] to yield 1.0 g of (3S, 4R)-4-cyano-3-(2-trimethylsilyl)-ethoxycarboxamido-2-azetidinone.

IR$\nu_{max}^{KBr}$cm$^{-1}$: 2950, 1885, 1710, 1510, 1250, 860, 840.

NMR(CDCl$_3$, ppm): 0.03 (s, CH$_3$), 1.00 (t, J=8 Hz, —CH$_2$—), 4.20 (t, J=8 Hz, —CH$_2$—), 4.60 (d, J=2 Hz, C$_4$—H), 5.33 (dd, J=2, 8 Hz, C$_3$—H), 5.70 (d, J=8 Hz, NH), 6.80 (br. s, NH)

EXAMPLE 9

In 50 ml of tetrahydrofuran was suspended 11.2 g of p-toluenesulfonate of (3S, 4RS)-3-amino-4-cyano-2-azetidinone. To the suspension was added under ice-cooling 5 g of triethylamine, which was stirred for 30 minutes, followed by concentration under reduced pressure. To the consentrate were added 20 ml of methylene chloride and 80 ml of propyleneoxide to make a solution. To the solution was added 6.8 g of carbobenzoxychloride under ice-cooling, which was stirred at 25° C. for 30 minutes, followed by concentration under reduced pressure. To the concentrate were added ethyl acetate and water, and the mixture was shake. The organic layer was taken, washed with water, and dried on anhydrous magnesium sulfate, followed by concentration under reduced pressure. The concentrate was purified on a 150 g silicagel column [developer, ethyl acetate:n-hexane (1:1)] to yield 2.1 g of (3S, 4R)-3-benzyloxycarboxamido-4-cyano-2-azetidinone as an oily substance and, subsequently, 3.21 g of (3S, 4S)-4-cyano-3-benzyloxycarboxamido-2-azetidinone as crystals.

(3S, 4S)-form.

mp 167°–170° C. (dec.).

IR$\nu_{max}^{KBr}$cm$^{-1}$: 3380, 3260, 2245, 1805, 1765, 1675, 1525

NMR(DMSO-d$_6$, ppm): 4.50 (d, J=5 Hz, C$_4$—H), 5.10 (s, —CH$_2$—), 5.16 (dd, J=8 Hz, C$_3$—H), 7.26 (s, arom H), 8.16 (d, J=8 Hz, NH), 8.56 (broad s, NH)

EXAMPLE 10

(1) In 15 ml of THF was dissolved 0.298 g of (3R, 4R)-3-benzyloxycarboxamido-4-methylsulfonyl-2-azetidinone. To the solution was added 0.25 g of palladium black, and the mixture was stirred for two hours in hydrogen streams. The catalyst was removed by filtration, and the filtrate was concentrated under reduced pressure until the volume was reduced to about 3 ml.

On the other hand, to 10 ml. of methylene chloride was added 0.555 g of 2-(2-chloroacetamidothizol-4-yl)-2-methoxyiminoacetic acid (syn-isomer). To the mixture were added, under ice cooling, 0.25 g of triethylamine, then 0.42 g of phosphorus pentachloride, and the whole mixture was stirred for five minutes, which was further stirred for 30 minutes at room temperature, followed by concentration under reduced pressure. The residue was washed with n-hexane to which was added 5 ml of THF, then resulting insolubles was removed by filtration. The filtrate was added, under ince-cooling, to a mixture of the solution prepared as above and 1 ml of propylene oxide. The solvent was removed by distillation, and the residue was dissolved in ethyl acetate. The ethyl acetate solution was washed with water, which was concentrated under reduced pressure. The concentrate was purified on a silicagel column [n-hexane-ethyl acetate (1:1)] to yield 0.13 g of (3R, 4R)-3-[2-(2-chloroacetamidothiazol-4-yl)-2-methoxyiminoacetamido-]-4-methylsulfonyl-2-azetidinone.

IR$\nu_{max}^{KBr}$cm$^{-1}$: 3370, 3270, 1790, 1680, 1540.

NMR(DMSO-d$_6$, ppm): 3.00 (s, CH$_3$), 3.93 (s, CH$_3$), 4.33 (s, —CH$_2$—), 4.93 (d, J=5 Hz, C$_4$—H), 5.57 (dd, J=5, 9 Hz, C$_3$—H), 7.53

(s, >—H), 8.30 (d, J=9 Hz, NH), 9.40 (s, NH), 12.73 (s, NH).

(2) In 3 ml of DMF was dissolved 0.46 g of (3R, 4R)-3-[2-(2-chloroacetamidothiazol-4-yl)-2-methoxyiminoacetamido]-4-methylsulfonyl-2-azetidinone. To this solution was added 0.36 g of a complex of sulfuric anhydride and pyridine, and the reaction was allowed to proceed for 12 days. To the reaction mixture was added ether, and the separating oily substance was washed with ether. The oily sustance was dissolved in water, to which was added 10 ml of sodium-type Dowex 50 W resin (manufactured by Dow Chemical Co.). The mixture was stirred for 30 minutes. The resin was removed by filtration, and the filtrate was purified on a column packed with AD-II resin (manufactured by Rohm & Hass Co.) to yield 0.023 g of sodium (3R, 4R)-3-[2-(2-chloroacetamidothiazol-4-yl)-2-methoxyiminoacetamido]-4-methylsulfonyl-2-azetidinone-1-sulfonate. IR$\nu_{max}^{KBr}$cm$^{-1}$: 3450–3400, 1785, 1685, 1672, 1280, 1260, 1052.

NMR (DMSO-d$_6$, ppm): 3.84 (s, CH$_3$), 4.33 (s, —CH$_2$—), 5.15 (d, J=5 Hz, C$_4$—H), 5.71 (dd, J=5, 9 Hz, C$_3$—H), 7.53

(s, >—H), 9.45 (d, J=9 Hz, NH), 12.88 (s, NH)

EXAMPLE 11

In 12 ml of tetrahydrofuran was dissolved 0.30 g of (3S, 4S)-3-amino-4-cyano-2-azetidinone.p-toluenesulfonate. To the solution were added, under ice-cooling, 0.12 g of triethylamine and, subsequently 0.60 g of 2-(2-chloroaceteamidothiazol-4-yl)-2-(1-p-nitrobenzyloxycarbonyl-1-methylethoxyimino)acetyl chloride hydrochloride. The mixture was stirred at room temperature for 40 minutes, followed by concentration under reduced pressure. The residue was purified on a silicagel column [ethyl acetate-chloroform-methanol (3:3:1)] to yield 0.27 g of (3S, 4S)-3-[2-(2-chloroacetamidothiazol-4-yl)-2-(1-p-nitrobenzeyloxycarbonyl1-methylethoxyimino)acetamideo]-4-cyano-2-azetidinone.

IR$\nu_{max}^{KBr}$cm$^{-1}$: 1785, 1740, 1675, 1530.

EXAMPLE 12

In 850 ml of an aqueous solution of tetrahydrofuran (1:1) was dissolved 100 g of p-tolunesulfonate of (3S, 4S)-3-amino-4-cyano-2-azetidinone. To the solution was added gradually, under stirring, 74.1 g of sodium hydrogen carbonate at a temperature not higher than 10° C. To the mixture was added carbobenzoxy chloride at 3°–5° C. in the course of 40 minutes, followed by stirring for 30 minutes at the same temperature. To the reaction mixture was added 300 ml. of ethyl acetate, and the mixture was shaken. The resulting ethyl acetate layer was separated. The aquenous layer was subjected to extraction with ethyl acetate. The extract solution was combined with the organic layer, washed with water, and dried on anhydrous magnesium sulfate, followed by concentration under reduced pressure. The precipitating crystals were collected by filtration to afford 34 g of (3S, 4S)-4-cyano-3-benzyloxycarboxamido-2-azetidinone. IR and NMR spectra of this compound are in agreement with those of the compound obtained in Example 9.

EXAMPLE 13

(1) To a solution of 12.3 g of (3R, 4S)-4-methylsulfonyl-3-tritylamino-2-azetidinone in 150 ml of DMF is added a solution of 1.6 g of potassium cyanide in 24 ml of water under ice-cooling and the mixture is stirred at room temperature (approx. 25° C.) for 30 minutes. To the reaction mixture are added ice water and ethyl acetate, and the ethyl acetate layer is taken, washed with water and dried over anhydrous magnesium sulfate. The solvent is then distilled off under reduced pressure and the residue is chromatographed on a silica gel column [eluant: ethyl acetate-n-hexane (1:1)] to give 6.7 g of (3S, 4RS)-4-cyano-3-tritylamino-2-azetidinone (4R:4S=1:1).

IR$\nu_{max}^{KBr}$cm$^{-1}$: 2230, 1770.

(2) To a solution of 10.6 g of (3S,4RS)-4-cyano-3-tritylamino-2-azetidinone thus obtained in 1) in 20 ml of acetone is added 6.3 g of p-toluenesulfonic acid monohydrate to give a uniform solution. The resultant crystalline precipitate is collected by filtration and washed with a small amount of acetone and ether. The filtrate is concentrated under reduced pressure and, on addition of acetone to the residue, a crystalline precipitate separates out, which is collected by filtration. The filtrate is concentrated and the residue treated in the same manner as above. There is obtained 3.4 g in total of (3S,4R)-3-amino-4-cyano-2-azetidinone p-toluenesulfonate (A). The filtrate is concentrated under reduced pressure, ether added to the residue, and the insoluble matter collected by filtration and washed with ether to give 4.1 g of (3S,4S)-3-amino-4-cyano-2-azetidinone p-toluenesulfonate containing about 10% of (3S,4R)-isomer.

(A):

IR$\nu_{max}^{KBr}$cm$^{-1}$:1770, 1200.

NMR (DMSO-d$_6$, ppm): 2.30 (s, CH$_3$), 4.55 (d, J=2 Hz, C$_4$—H), 4.95 (d, J=2 Hz, C$_3$—H), 7.03 (d, J=8 Hz, arom H), 7.46 (d, J=8 Hz, arom H), 8.30 ~9.00 (broad. NH$_2$), 9.46 (broad s, NH).

(B):

IR$\nu_{max}^{KBr}$cm$^{-1}$:1800, 1180.

EXAMPLE 14

(1) To a mixture of 1.10 g of (3S,4RS)-4-cyano-3-tritylamino-2-azetidinone, 0.50 g of triethylamine and 20 ml of methylene chloride is added 0.56 g of tert-butyldimethylsilyl chloride under ice-cooling and stirring. The mixture is stirred at room temperature (approx. 25° C.) for 30 minutes and the reaction mixture is concentrated under reduced pressure. The residue is chromatographed on a a silicagel column [eluant: ethyl acetate-n-hexane (1:3)] to give 0.64 g of (3S,4RS)-1-tert-butyldimethylsilyl-4-cyano-3-tritylamino-2-azetidinone.

IR$\nu_{max}^{KBr}$cm$^{1}$: 2950, 2240, 1760, 1260. NMR (CDCl$_3$, ppm): 0.13 (s, CH$_3$), 0.80 (s, t-Bu), 3.03 (d, J=2Hz, C$_4$—H), 3.10 (d,J=8 Hz, NH), 3.43 (d, J=5 Hz, C$_4$—H), 4.46 (dd, J=2, 5 Hz, C$_3$—H), 4.50 (dd, J=5, 8 Hz, C$_3$—H), 7.00~7.50 (m, arom H).

(2) A mixture of 0.469 g of the 4-cyano compound thus obtained in (1) above, 5 ml of methanol, 0.33 ml of 30% aqueous hydrogen peroxide and 1 ml of 1 N sodium hydroxide is stirred at room temperature (approx. 25° C.) for 4 hours. The reaction mixture is concentrated under reduced pressure and ethyl acetate and saturated aqueous sodium chloride are added to the residue. The organic layer is separated, dried over anhydrous magnesium sulfate and concentrated under reduced pressure. The residue is chromatographed on a silicagel column (eluant: ethyl acetate) to give 0.557 g of (3S,4RS)-4-carbamoyl-3-tritylamino-2-azetidinone (1:1 4R-4S mixture).

IR$\nu_{max}^{KBr}$cm$^{-1}$: 1750, 1670

NMR(DMSO-d$_6$+D$_2$O, ppm): 3.46 (d, J=4 Hz, C$_4$—H), 3.56 (d, J=2 Hz, C$_4$—H), 4.08 (d, J=2 Hz, C$_3$—H), 4.26 (d, J=4 Hz, C$_3$—H), 7.2~7.7 (m, arom H)

EXAMPLE 15

(1) To a solution of 6 g of (3S,4S)-4- acetoxy-3-benzyloxycarboxamido-2-azetidinone in 30 ml of dimethylformamide is added a solution of 1.5 g of potassium cyanide in 5 ml of water under ice-cooling. The mixture is stirred at room temperature (approx. 25° C.) for 30 minutes, poured into ice water and extracted with ethyl acetate. The ethyl acetate layer is washed with water, dried over anhydrous magnesium sulfate and concentrated under reduced pressure. The residue is dissolved in 30 ml of methylene chloride and, following addition of 2.2 g of triethylamine, 3.2 g of tert-butyldimethylsilyl chloride is added under ice-cooling. The mixture is stirred at room temperature for 30 minutes and concentrated under reduced pressure. The residue is chromatographed on a silica gel column [eluant: ethyl acetate-n-hexane (1:1)] to give 0.300 g of (3S,4R)-3-benzyloxycarboxamido-1-tert-butyldimethylsilyl-4-cyano-2-azetidinone.

IR$\nu_{max}^{film}$ cm$^{-1}$: 2950, 2920, 2140, 1745, 1720, 1250.

NMR (CDCl$_3$, ppm): 0.06 (s, CH:$_3$), 0.90 (s, t-Bu), 4.36 (d, J=2 Hz, C$_4$—H), 4.70 (dd, J=2, 8 Hz, C$_3$—H), 5.02 (s, —CH$_2$—), 5.46 (d, J=8 Hz, NH), 7.28 (s, arom H)

(2) In 5 ml of ethanol is dissolved 0.003 g of the 4-cyano compound thus obtained (1) above and, under ice-cooling, 0.3 ml of 30% aqueous hydrogen peroxide and 0.15 ml of 1 N sodium hydroxide are added. The mixture is stirred at room temperature (approx. 25° C.) for an hour and concentrated under reduced pressure. The residue is shaken with ethyl acetate and water, and the ethyl acetate layer is separated, dried over anhydrous magnesium sulfate and concentrated under reduced pressure. The residue is chromatographed on a silica gel column [eluant: ethyl acetate] to give 0.04 g of (3S,4R)-3-benzyloxycarboxamido4-carbamoyl-2-azetidinone.

mp 158°~155° C. (dec.). IR$\nu_{max}^{KBr}$cm$^{-1}$: 1770, 1705, 1690, 1665, 1520, 1250.

NMR (DMSO-d$_6$, ppm): 3.91 (d, J=2 Hz, C$_4$—H), 4.42 (dd, J=2, 8 Hz), C$_3$—H), 5.06 (s, —CH$_2$—), 7.18, 7.60 (each br s, CONH$_2$), 7.36 (s, arom H), 8.04 (d, J=8 Hz, NH), 8.30 (br s, NH)

EXAMPLE 16

In 1 ml of dimethyl sulfoxide is dissolved 122 mg of (3S,4S)-3-benzyloxycarboxamido-4-cyano-2-azetidinone and, under stirring at 20° C., 0.1 ml of 30% aqueous hydrogen peroxide and then 0.1 ml of 1 N sodium hydroxide are added. After 10 minutes, the crystalline precipitate is collected by filtration, washed a small amount of 99% ethanol and dried to give 42 mg of (3S,4S)-3-benzyloxycarboxamido-4-carbamoyl-2- azetidinone. The filtrate is chromatographed on an XAD-II column (eluant: 30% aqueous ethanol) to give 37 mg of (3S,4S)-3-benzyloxycarboxamido-4-carbamoyl-2-azetidinone as a further crop.

mp 236°~240° C. (dec.).

$[\alpha]_D^{20}+10.43$ (DMSO, c=1).

$IR\nu_{max}^{KBr}cm^{-1}$: 3400, 3310, 1775, 1740, 1675, 1545

NMR (DMSO, ppm): 4.14 (d, J=5 Hz, $C_4$—H), 5.06 (s, —$CH_2$—), 5.08 (dd, J=5, 8 Hz, $C_3$—H), 7.30 (broad s, $NH_2$), 7.35 (s, arom H), 7.52 (d, J=8 Hz, NH), 8.33 (broad s, NH).

EXAMPLE 17

In 12 ml of dichloromethane is dissolved 1.06 g of (3S,4S)-4-cyano-3-triphenylmethylamino-2-azetidinone and, following addition of 1.02 g of tetra-n-butylammonium hydrogen sulfate, 0.68 ml of 30% aqueous hydrogen peroxide and 4.5 ml of 1 N sodium hydroxide are added under ice-cooling and stirring. The mixture is stirred vigorously for 50 minutes and poured into ice water containing 1.3 ml of 1 N hydrochloric acid. After phase separation, the aqueous layer is extracted twice with chloroform. The organic layers are combined and washed with an aqueous solution of sodium thiosulfate and sodium chloride, dried over magnesium sulfate, and concentrated under reduced pressure. The residue is chromatographed on a silica gel column [eluant: chloroform-ethyl acetate-methanol (50:50:5)] to give 0.223 g of (3S,4S)-4-carbamoyl-3-triphenylmethylamino-2-azetidinone.

$IR\nu_{max}^{Kbr}cm^{-1}$: 3370, 1750, 1675, 705.

NMR (DMSO-$d_6$, ppm): 3.44 (d, J=5 Hz, $C_4$—H), 3.55 (d, J=10 Hz, NH), 4.10 (dd, J=5, 10 Hz, $C_3$—H), 6.90 (broad s, $NH_2$), 7.0–7.6 (m, arom H), 7.89 (s, NH).

EXAMPLE 8

In 2 ml of dimethyl sulfoxide is dissolved 0.38 g of (3S,4S)-3-[2-(2-chloroacetamidothiazol-4-yl)-2-(1-p-nitrobenzyloxycarbonyl-1-methylethoxyimino)acetamido]-4-cyano-2-azetidinone and, following addition of 0.1 ml of 30% aqueous hydrogen peroxide and 0.1 ml of 1 N sodium hydroxide, the mixture is stirred at approx. 25° C. for 30 minutes. The reaction mixture is chromatographed on an XAD-II column (eluant: 30% ethanol) to give 0.12 of (3S,4S)-4-carbamoyl-3-[2-(2-chloroacetamidothiazol-4-yl)-2-(1-p-nitrobenzyloxycarbonyl-1-methylethoxyimino)acetamido]-2-azetidinone.

$IR\nu_{max}^{KBr}cm^{-1}$: 1760, 1750, 1680, 1520, 1350.

NMR (DMSO-$d_6$, ppm): 1.52 (s, $CH_3$), 4.27 (d, J=6 Hz, $C_4$—H), 4.34 (s, $ClCH_2$—), 5.32 (s, —$CH_2$—), 5.46 (dd, J=6, 9 Hz, $C_3$—H), 7.41

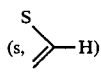

7.60, 8.08 (d, J=9 Hz, arom H), 8.47 (s, NH), 8.86 (d, J=9Hz, NH)

EXAMPLE 19

In 2 ml of dichloromethane is dissolved 160 mg of (3S,4S)-4-cyano-3-triphenylmethylamino-2-azetidinone and, following addition of 154 mg of tetra-n-butylammonium hydrogen sulfate, 0.103 ml of 30% aqueous peroxide and 0.68 ml of 1 N sodium hydroxide are added under ice-cooling and stirring. The mixtire is stirred vigorously for 30 minutes and poured into ice water containing 0.22 ml of 1 N hydrochloric acid. After phase separation, the aqueous layer is extracted twice with chloroform. The organic layers are combined, washed with aqueous sodium chloride, dried over magnesium sulfate and concentrated under reduced pressure. The residue is chromatographed on a silica gel column [eluant: chloroform-ethyl acetate-methanol (50:50:5)] to give 75 mg of (3S,4S)-4-carbamoyl-3-triphenylmethylamino-2-azetidinone. The IR and NMR spectra of this compound are identical with those of the compound obtained in Example 17.

EXAMPLE 20

In 120 ml of carbon tetrachloride are dissolved 12.2 g of (3R,4R)-4-methylsulfonyl-3-tritylamino-2-azetidinone and 2.44 g of tri-n-octlymethylammonium chloride and, under stirring, a solution of 2.15 g of potassium cyanide in 30 ml of water is added. The mixture is stirred vigorously at the same temperature for 15 minutes and the organic layer is separated, while the aqueous layer is extracted with chloroform. The organic layers are combined, washed with water and treated in the same manner as (1) of Example 13 to give 7.66 g of (3S,4RS)-4-cyano-3-tritylamino-2-azetidinone.

This compound is a 1:1 mixture of (3S,4R) and (3S,4S) forms.

(3S,4R) compound:

NMR (CDCl$_3$, ppm): 2.94 (d, J=11 Hz, Tr (trityl)-N,uns/H/ —), 3.00 (d, J=2 Hz, $C_4$—H), 4.64 (dd, J=2, 11 Hz, $C_8$—H), 6.40 (s, NH), 7.1~7.7 (m, arom H).

(3S,4S) compound:

NMR (CDCl$_3$, ppm): 3.17 (d, J=11 Hz, TrNH—), 3.56 (d, J=5 Hz, $C_4$—H), 4.64 (dd, J=5, 11 Hz, $C_3$—H), 6.30 (s, NH), 7.1~7.7 (m, arom H).

EXAMPLE 21

In 40 ml of chloroform is dissolved 3.54 g of (3R,4RS)-4-cyano-3-tritylamino-2-azetidinone as obtained in Example 20 and, following addition of 3.4 g of tetra-n-butylammonium hydrogen sulfate, 2.3 g of 30% hydrogen peroxide and 15 ml of 1 N sodium hydroxide are added under ice-cooling and stirring. The mixture is stirred vigorously for 30 minutes and the organic layer is taken out, while the aqueous layer is extracted twice with chlorform. The organic layers are combined, washed with water and treated in the same manner as Example 19 to give 0.76 g of (3S,4S)-4-carbamoyl-3-trityl-amino-2-azetidinone. The IR and NMR spectra of this compound are identical with those of the compound obtained in Example 17.

EXAMPLE 22

In 2 ml of benzene are dissolved 0.5 mmol of (3R,4R)-4-methylsulfonyl-3-tritylamino-2-azetidinone and 0.1 mmol of tetra-n-amylammonium bromide, and a solution of 0.55 mmol of potassium cyanide in 0.55 ml of water is added at 15° C. The mixture is stirred vigorously for 15 minutes and treated in the same manner as Example 20 to give (3S,4RS)-4-cyano-3-tritylamino-2-azetidinone with the (3R,4R):(3S,4S) ratio of 1:4.

EXAMPLE 23

Using benzyltriethylammonium chloride instead of tetra-n-amylammonium bromide, the procedure of Example 22 is repeated to give (3S,4RS)-4-cyano-3-tritylamino-2-azetidinone (4R:4S=1:3.5).

EXAMPLE 24

Using tetra-n-butylphosphonium instead of tetra-n-amylammonium bromide, the procedure of Example 22 is repeated to give (3R,4RS)-4-cyano-3-tritylamino-2-azetidinone (4R:3S=1:3.5).

Reference Example (1) In 2 ml of dry N,N-dimethylformamide is dissolved 630 mg of (3S,4S)-4-carbamoyl-3-[2-(2-chloroacetamidothiazol-4-yl)-2-(1-p-nitrobenzyloxycarboxyl-1-methylethoxyimino)acetamido]-2-azetidinone (syn-isomer) as obtained in Example 18. Then, at −78° C., 1.69 ml of sulfuric anhydride-N, N-dimethylformamide complex solution (1.56 M) is added. The mixture is allowed to stand at 4° C. in a refrigerator overnight. To this reaction mixture are added 208 mg of pyridine under ice-cooling and then 30 ml of ether, and the resultant syrupy precipitate is washed with ether by the decantation method (20 ml×3). The precipitate is dissolved in 15 ml of water, and after addition of 15 ml of Dowex 50W (Na-form) resin, the mixture is stirred at room temperature for 2 hours. The resin is filtered off and the filtrate is concentrated under reduced pressure. The residue is chromatographed on an Amberlite XAD-II column and serial eultion is carried out with water and 10–20% ethanol to give the 1,4-disulfo compound, followed by further elution with 40% ethanol. The fraction of 40% ethanol including desired compound is lyophilized to give 480 mg of sodium (3S,4)-4-carbamoyl-3[2-(2-chloracetamidothiazol-4-yl)-2-(1-p-nitrobenzyloxycarbonyl-1-methylethoxyimino)acetamido]-2-azetidinone-1-sulfonate (syn-isomer).

(2) In 20 ml of water is dissolved 480 mg of sodium (3S,4S)-4-carbamoyl-3-[2-(2-chloroacetamidothiazo-4-yl)-2-(1-p-nitrobenzyloxycarbonyl-1-methylethoxyimino)acetamido]-2-azetidinone-1-sulfonate (syn-isomer) as obtained in the above (1) and under ice-cooling and stirring, 104 mg of sodium monomethyldithiocarbamate is added. The mixture is stirred at room temperature for 1.5 hours. The reaction mixture is twice washed with ether, and then purified by column chromatography on Amberlite XAD-II (40 g), eluting with water and then 20% ethanol. The fractions including the desired product are combined and lyophilized to give 300 mg of sodium (3S,4S)-4-carbamoyl-3-[2-2-aminothiazol-4-yl)-2-(1-nitrobenzyloxycarbonyl-1-methylethoxyimino)acetamido]-2-azetidinone-1-sulfonate (syn-isomer).

(3) In 10 ml of water is dissolved 300 mg of sodium (3S,4S)-4-carbamoyl-3-[2-(2-aminothiazol-4-yl)-2-(1-p-nitrobenzyloxycarbonyl-1-methylethoxyimino)acetamido]-2-azetidinone-1-sulfonate (syn-isomer) as obtained in the above (2), followed by addition of 300 mg of 10% palladium- on-carbon. The mixture is stirred in a hydrogen atmosphere at room temperature for one hour. The catalyst is filtered off, and under ice-cooling 27 mg of sodium hydrogen carbonate is added. The mixture is stirred for 5 minutes and washed with ethyl acetate. To the aqueous layer is added 30 ml of Dowex 50W (H-form) resin, and the mixture is stirred for 1.5 hours. The resin is filtered off and the filtrate is concentrated under reduced pressure to about a half volume thereof. The residue is chromatographed on an Amberlite XAD-II (40 g) column, eluting with water and then 15% ethanol. The fractions including the desired product are combined and lyophilized to give 150 mg of (3S,4S)-4-carbamoyl-3-[2-(2-aminothiazol-4-yl)-2-(1-methyl-1-carboxyethoxyimino)acetamido]-2-azetidinone-1-sulfonic acid (syn-isomer).

$[\alpha]_D^{23} - 37.8°$ (C=1.01, H$_2$O)

Anal. Calcd. for $C_{13}H_{16}N_6O_9S_2 2^{1/2}H_2O$: C,30.65; H, 4.15; N,16.50. Found: C, 30.74; H, 4.27; N, 16.55.

IR $\nu_{max}^{KBr}$ cm$^{-1}$: 3340, 1770, 1720, 1680, 1635, 1275, 1050.

NMR (d$_6$-DMSO, ppm): 1.52 (6H, S, 2×CH$_3$), 4.78 (1H, d, J=6 Hz, C$_4$—H), 5.33 (1H, d,d, J=6, 9 Hz, C$_3$—H), 7.20

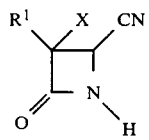

(1H, S, ), 7.29-7.59 (2H, CONH$_2$), 9.19 (1H, d, J=9 Hz, C$_3$—NH).

Industrial Utility

4-Cyano-2-azetidinone derivatives [I] are useful as advantageous intermediates in the synthesis of optically active 4-substituted-2-azetidinone derivatives having excellent antimicrobial and beta-lactamase inhibiting activities. When W is a sulfo group, [I] per se have antimicrobial and beta-lactamase inhibiting activities and are useful as therapeutic agents for treating infectious diseases caused by gram-positive or negative bacteria in humans and mammals including dogs, cats, cattle, horses, mice and guinea pigs, as preservatives for animal feed and industrial water, or as disinfectants for sanitary tools and appliances, and further as degradation inhibitors for beta-lactam antibiotics in combined use thereof with said antibiotics.

What we claim is:

1. A 4-cyano-2-azetidinone compound of the formula

wherein X is hydrogen atom or methoxy; and R$^1$ is
(1) amino,
(2) an acylated amino group wherein the acyl moiety is
(A) a group of the formula:

R$^5$—CO$_{13}$ wherein R$^5$ is lower alkyl other than C$_{1-5}$ alkyl-CH$_2$—, phenyl* or heterocyclic* group;
(B) a group of the formula:

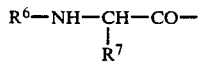

wherein R$^6$ is hydrogen, amino acid residue*, amino-protecting group or a group R$^8$—(CH$_2$)$_m$—CO—wherein R$^8$ is heterocyclic*, phenyl* or lower alkyl*; m is an integer of 0 to 3; R$_7$ is hydrogen, lower alkyl*, phenyl*, heterocyclic* or cycloalkenyl*;
(C) a group of the formula:

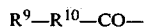

$$R^9-R^{10}-CO-$$

wherein $R^9$ is a group

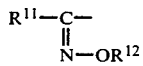

wherein $R^{11}$ is heterocyclic* or phenyl*; $R^{12}$ is hydrogen, phenyl*, lower acyl or lower alkyl or a group $-R^{13}-R^{14}$ where $R^{13}$ is lower alkylene or lower alkenylene and $R^{14}$ is carboxyl or esterified carboxyl; $R^{10}$ is a direct bond or a group

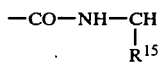

wherein $R^{15}$ is lower alkyl or heterocyclic*;
(D) a group of the formula:

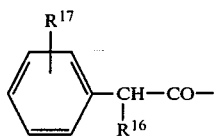

wherein $R^{16}$ is halogen, hydroxy, carboxyl, sulfo, formyloxy or azido; $R_{17}$ is hydrogen, halogen, lower alkyl, lower alkoxy or hydroxy; or
(E) a group of the formula:

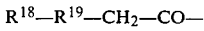

$$R^{18}-R^{19}-CH_2-CO-$$

wherein $R^{18}$ is cyano, phenyl*, phenoxy*, lower alkyl*, alkenyl* or heterocyclic*; $R^{19}$ is a direct bond or $-S-$; and, in the symbols $R^5$ through $R^{19}$,
(a) the lower alkyl is a $C_{1-6}$ alkyl,
(b) the lower alkoxy is a $C_{1-6}$ alkoxy,
(c) the alkenyl group contains 2–4 carbon atoms,
(d) the cycloalkenyl is of 5- or 6-carbon atoms,
(e) the lower alkylene contains 1–3 carbon atoms,
(f) the lower alkenylene contains up to 3 carbon atoms,
(g) the halogen atom is chlorine, bromine, iodine or fluorine,
(h) the heterocyclic group is 2- or 3-pyrrolyl, 2- or 3-furyl, 2- or 3-thienyl, 2- or 3-pyrrolidinyl, 2-, 3- or 4-pyridyl, N-oxido-2-, 3- or 4-pyridyl, 2-, 3- or 4-piperidinyl, 2-, 3- or 4-pyranyl, 2-, 3- or 4-thiopyranyl, pyrazinyl, 2-, 4- or 5-thiazolyl, 2-, 4- or 5-oxazolyl, 3-, 4- or 5-isothiazolyl, 3-, 4- or 5-isoxazolyl, 2-, 4- or 5-imidazolyl, imidazolidinyl, 3-, 4- or 5-pyrazolyl, pyrazolidinyl, 3- or 4-pyridazinyl, N-oxido-3- or 4-pyridazinyl, 2-, 4- or 5-pyrimidinyl, N-oxido-2-, 4- or 5-pyrimidinyl, piperazinyl, 4- or 5-(1,2,3-thiadiazolyl), 3- or 5-(1,2,4-thiadiazolyl), 1,3,4-thiadiazolyl, 1,2,5-thiadiazolyl), 4- or 5-(1,2,3-oxadiazolyl), 3- or 5-(1,2,4-oxadiazolyl), 1,3,4-oxadiazolyl, 1,2,5-oxadiazolyl, 1,2,3- or 1,2,4-triazolyl, 1H- or 2H-tetrazolyl, pyrido(2,3-d)pyrimidyl, benzopyranyl, 1,8-, 1,5-, 1,6-, 1,7-, 2,7- or 2,6-naphthyridyl, quinolyl or thieno(2,3-b)pyridyl,
(i) the amino acid residue is glycyl, alanyl, valyl, leucyl, isoleucyl, seryl, threonyl, cysteinyl, cystyl, methionyl, α-, or β-aspartyl, α- or β-glutamyl, lysyl, arginyl, phenylalanyl, phenylglycyl, tyrosyl, histidyl or tryptophyl,
(j) the lower acyl group contains 2–4 carbon atoms,
(k) the group with a superscript asterisk "*" is unsubstituted or substituted with one to three substituents which may be the same or different, wherein the amino, carboxyl and hydroxy group may be protected, thus the substituent of the substituted lower alkyl and of the substituted alkenyl is phenyl, carbamoyl, methylcarbamoyl, carboxy, cyano, halogen or hydroxy, the substituent of the substituted phenyl, phenoxy and cycloalkenyl is $C_{1-3}$ alkyl, $C_{1-3}$ alkoxy, halogen, amino, benzyloxy, hydroxy, $C_{2-10}$ acyloxy, aminomethyl, carbamoylaminomethyl or 3-amino-3-carboxypropoxy, the substituent of the substituted heterocyclic group is $C_{1-8}$ alkyl, $C_{1-3}$ alkoxy, hydroxy, carboxyl, oxo, monochloroacetamido, aldehyde, trifluoromethyl, amino, halogen, coumarin-3-carbonyl, 4-formyl-1-piperazinyl, pyrrolealdimino, furanaldimino, thiophenealdimino, mesyl, mesylamino-, amino-protecting group, halo-substituted $C_{2-4}$ acylamino, phenyl or phenyl substituted with one to three substituents selected from $C_{1-3}$ alkyl, $C_{1-3}$ alkoxy, halogen, amino, benzyloxy, hydroxy, $C_{2-10}$ acyloxy, aminomethyl, carbamoylaminomethyl and 3-amino-3-carboxypropyl, and the substituent of the substituted amino acid residue is amino, amino-protecting group, carbamoyl, methylcarbamoyl or benzyl, or
(3) an amino protected with phthaloyl, p-tert-butylbenzenesulfonyl, benzenesulfonyl, toluenesulfonyl, methanesulfonyl, ethanesulfonyl, succinyl, methoxycarbonyl, ethoxycarbonyl, t-butoxycarbonyl, isopropoxycarbonyl, 2-cyanoethoxycarbonyl, β,β,β-trichloroethoxycarbonyl, β-trimethylsilylethoxycarbonyl, β-methylsulfonylethoxycarbonyl, benzyloxycarbonyl, p-nitrobenzyloxycarbonyl, p-methoxybenzyloxycarbonyl, di-phenylmethyloxycarbonyl, methoxymethyloxycarbonyl, acetylmethyloxycarbonyl, isobornyloxycarbonyl, phenyloxycarbonyl, trityl, 2-nitrophenylthio, benzylidene, 4-nitrobenzylidene, trialkylsilyl, benzyl or p-nitrobenzyl, or an acid-addition salt thereof.

2. A compound as claimed in claim 1, wherein $R_1$ is an acylated amino group (2) as defined in claim 1.

3. A compound as claimed in claim 1, wherein $R_1$ is an acylated amino group, the acyl moiety of which is
(A) a group of the formula:

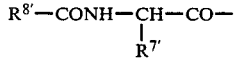

$$R^{8'}-CONH-CH-CO-$$
$$\phantom{R^{8'}-CONH-}R^{7'}$$

wherein $R^{7'}$ and $R^{8'}$ are heterocyclic* groups; or
(B) a group of the formula:

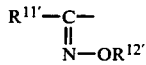

wherein $R^{11'}$ is a heterocyclic* group and $R^{12'}$ is lower alkyl; and in symbols $R^{7'}$ and $R^{9'}$ and $R^{11'}$ the heterocyclic group is as defined in claim 1 in symbol $R^{12'}$ the lower alkyl is a $C_{1-6}$ alkyl, and the group with a superscript asterisk "*" is unsubstituted or substituted with one to three substituents selected from $C_{1-8}$ alkyl, $C_{1-3}$ alkoxy, hydroxy, carboxyl, oxo, monochloroacetamido, aldehyde, trifluoromethyl, amino, halogen, coumarin-3-carbonyl, 4-formyl-1-piperazinyl, pyrrolealdoimino, furanaldoimino, thiophenealdoimino, mesyl, mesylamino, aminoprotecting group, halo-substituted $C_{2-4}$ acylamino, phenyl or phenyl substituted with one to three substituents selected from $C_{1-3}$ alkyl, $C_{1-3}$ alkoxy, halogen, amino, benzyloxy, hydroxy, $C_{2-10}$ acyloxy, aminomethyl, carbamoylaminomethyl and 3-amino-3-carboxypropyl.

4. A compound as claimed in claim 1, wherein the cyano group has cis configuration to the group $R^1$ having $\beta$-configuration to the azetidine ring.

5. A compound as claimed in claim 1, which is 4-cyano-3-tritylamino-2-azetidinone.

6. A compound as claimed in claim 1, which is 3-amino-4-cyano-2-azetidinone.

7. A compound as claimed in claim 5, which has (3S, 4RS) configuration.

8. A compound as claimed in claim 6, which has (3S, 4R) configuration.

9. A compound as claimed in claim 6, which has (3S, 4S) configuration.

* * * * *

UNITED STATES PATENT AND TRADEMARK OFFICE
CERTIFICATE OF CORRECTION

PATENT NO.   : 4,560,508
DATED        : December 24, 1985
INVENTOR(S)  : TAISUKE MATSUO, MICHIHIKO OCHIAI and
               SHOJI KISHIMOTO It is certified that error appears in the above-identified patent and that said Letters Patent is hereby corrected as shown below:

Column 30, line 55, change "$R^5-CO_{13}$" to --$R^5$-CO- --.

Signed and Sealed this

Twentieth Day of May 1986

[SEAL]

Attest:

DONALD J. QUIGG

Attesting Officer

Commissioner of Patents and Trademarks